US011540956B2

(12) United States Patent
Takeuchi

(10) Patent No.: US 11,540,956 B2
(45) Date of Patent: Jan. 3, 2023

(54) DISPOSABLE WEARING ARTICLE WITH IMPROVED AIR PERMEABILITY AND MANUFACTURING METHOD THEREFOR

(71) Applicant: Daio Paper Corporation, Ehime (JP)

(72) Inventor: Tomonari Takeuchi, Tochigi (JP)

(73) Assignee: Daio Paper Corporation, Ehime (JP)

( * ) Notice: Subject to any disclaimer, the term of this patent is extended or adjusted under 35 U.S.C. 154(b) by 937 days.

(21) Appl. No.: 16/333,645

(22) PCT Filed: Jul. 19, 2017

(86) PCT No.: PCT/JP2017/026043
§ 371 (c)(1),
(2) Date: Mar. 15, 2019

(87) PCT Pub. No.: WO2018/061419
PCT Pub. Date: Apr. 5, 2018

(65) Prior Publication Data
US 2019/0254885 A1 Aug. 22, 2019

(30) Foreign Application Priority Data

Sep. 30, 2016 (JP) .............................. JP2016-194293

(51) Int. Cl.
*A61F 13/49* (2006.01)
*A61F 13/15* (2006.01)
(Continued)

(52) U.S. Cl.
CPC .......... *A61F 13/49012* (2013.01); *A61F 5/44* (2013.01); *A61F 13/15* (2013.01);
(Continued)

(58) Field of Classification Search
None
See application file for complete search history.

(56) References Cited

U.S. PATENT DOCUMENTS 4,938,759 A * 7/1990 Enscore ............... A61K 9/7092
604/890.1
5,151,092 A * 9/1992 Buell .................. A61F 13/4902
604/385.3

(Continued)

FOREIGN PATENT DOCUMENTS

JP H09285487 4/1997
JP H11216163 5/1998
(Continued)

OTHER PUBLICATIONS

International Search Report, PCT/JP2017/026043, dated Aug. 29, 2017.
(Continued)

*Primary Examiner* — Michele M Kidwell
(74) *Attorney, Agent, or Firm* — Andrus Intellectual Property Law, LLP

(57) ABSTRACT

An elastic film stretchable structure in which an elastic film is stacked between a first sheet layer having air permeability and a second sheet layer having air permeability, the first sheet layer and the second sheet layer are bonded through bonding holes penetrating the elastic film at a number of sheet bonded portions arranged at intervals. A region having the elastic film stretchable structure has a stretchable region that is stretchable in a stretchable direction, and the stretchable region is contracted in the stretchable direction by a contraction force of the elastic film and is extensible in the stretchable direction, and vent holes are formed on the elastic film at sites where the elastic film does not overlap with the sheet bonded portions.

10 Claims, 23 Drawing Sheets

(51) Int. Cl.
  *A61F 13/496* (2006.01)
  *A61F 13/51* (2006.01)
  *B32B 7/08* (2019.01)
  *B32B 5/12* (2006.01)
  *A61F 5/44* (2006.01)

(52) U.S. Cl.
  CPC ........ *A61F 13/15739* (2013.01); *A61F 13/49* (2013.01); *A61F 13/496* (2013.01); *A61F 13/51* (2013.01); *B32B 5/12* (2013.01); *B32B 7/08* (2013.01); *A61F 2013/15552* (2013.01)

(56) References Cited

U.S. PATENT DOCUMENTS

| | | | |
|---|---|---|---|
| 5,567,501 A * | 10/1996 | Srinivasan | D04H 1/558 428/137 |
| 6,830,800 B2 | 12/2004 | Curro et al. | |
| 6,884,494 B1 | 4/2005 | Curro et al. | |
| 10,849,797 B2 * | 12/2020 | Sakai | A61F 13/15739 |
| 11,045,360 B2 * | 6/2021 | Furuhashi | A61F 13/49 |
| 11,103,389 B2 * | 8/2021 | Takahashi | B29C 66/81433 |
| 2002/0016122 A1 * | 2/2002 | Curro | A61F 13/15593 428/103 |
| 2010/0051170 A1 * | 3/2010 | Nakakado | A61F 13/15739 156/73.1 |
| 2010/0215923 A1 * | 8/2010 | Frost | B29C 66/21 428/196 |
| 2018/0014979 A1 * | 1/2018 | Fujita | B29C 66/81429 |
| 2018/0014984 A1 * | 1/2018 | Sakai | B29C 66/21 |
| 2018/0015709 A1 | 1/2018 | Takeuchi | |
| 2018/0028371 A1 * | 2/2018 | Takaishi | A61F 13/51464 |
| 2018/0078429 A1 * | 3/2018 | Matsumura | A61F 13/15 |
| 2019/0133846 A1 * | 5/2019 | Shirai | A61F 13/15699 |
| 2019/0167487 A1 * | 6/2019 | Takeuchi | B29C 66/344 |
| 2021/0069029 A1 * | 3/2021 | Sakai | B29C 66/81429 |

FOREIGN PATENT DOCUMENTS

| | | |
|---|---|---|
| JP | 2004532758 | 10/2004 |
| JP | 2006240301 | 9/2006 |
| JP | 2008136794 | 6/2008 |
| WO | 2001024755 | 4/2001 |
| WO | 2012/036599 | 3/2012 |
| WO | 2016/121976 | 8/2016 |
| WO | 2016121981 | 8/2016 |

OTHER PUBLICATIONS

Extended European Search Report for EP 17855377.2, dated Mar. 12, 2020.

* cited by examiner

FIG.12
(a)
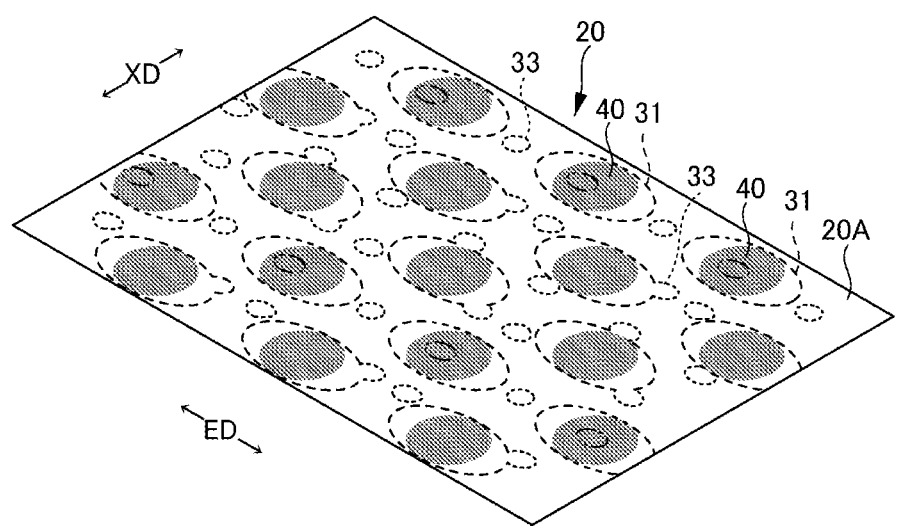
(b)
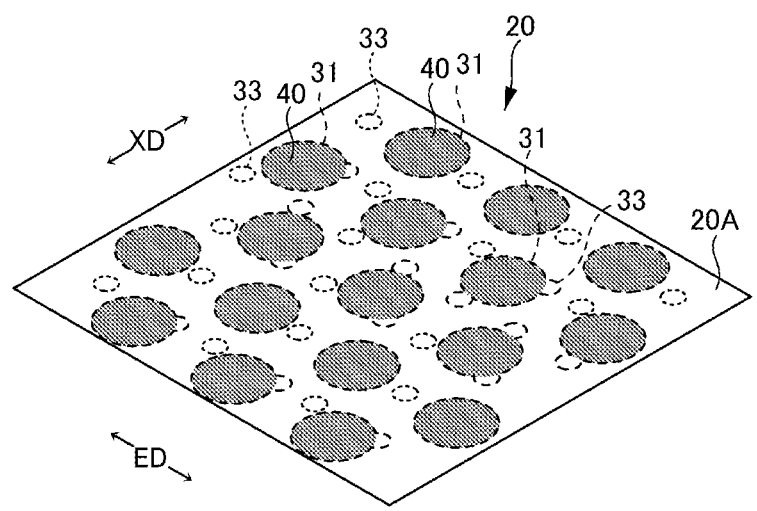

FIG.17
(a)
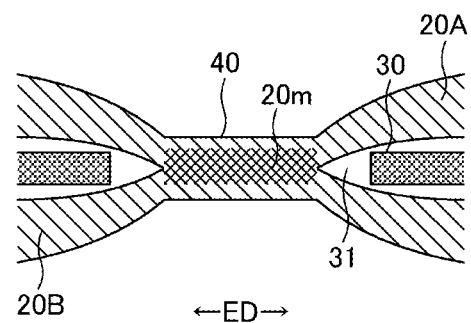
(b)
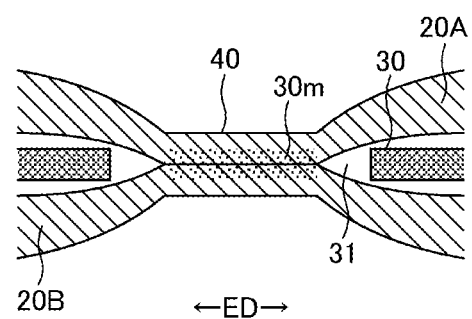
(c)
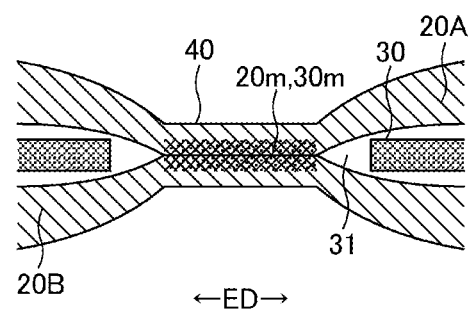

FIG.18
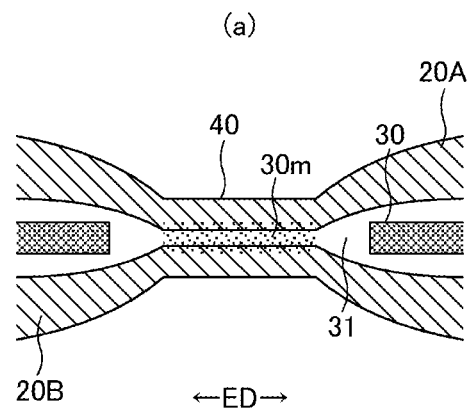
(a)
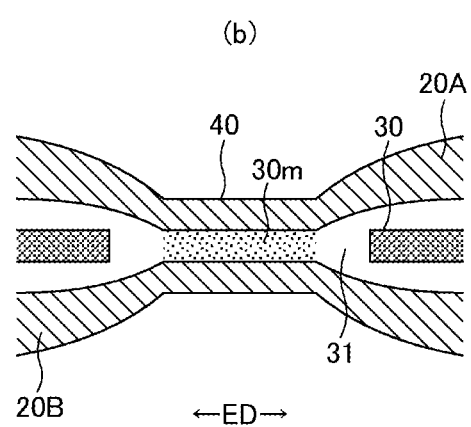
(b)
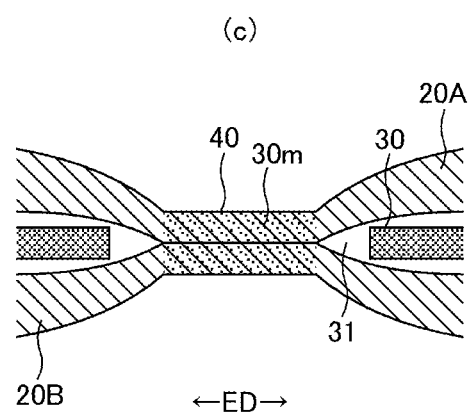
(c)

FIG.19
(a)
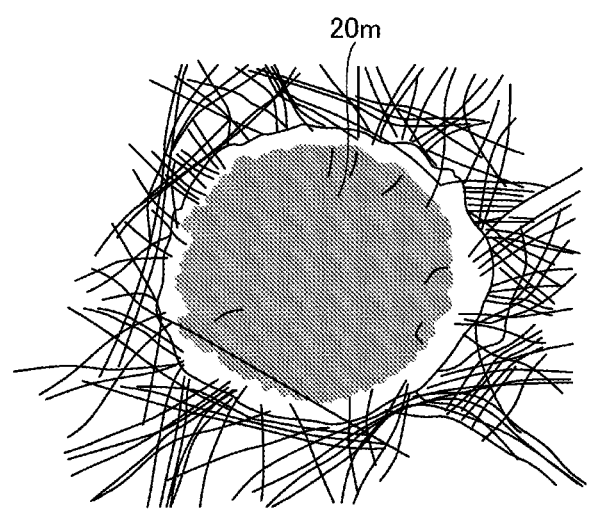
(b)
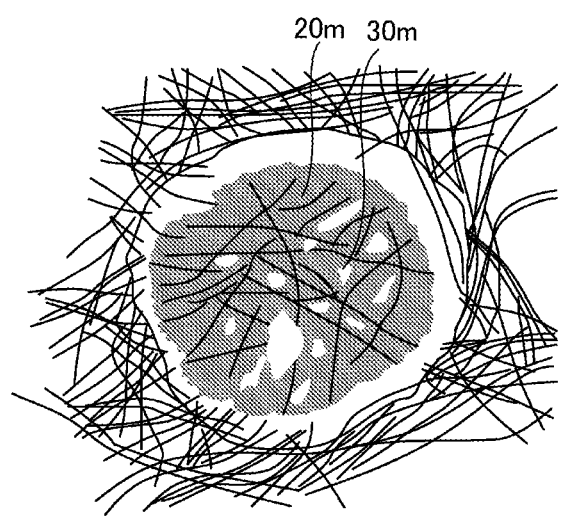

DISPOSABLE WEARING ARTICLE WITH IMPROVED AIR PERMEABILITY AND MANUFACTURING METHOD THEREFOR

CROSS-REFERENCE TO RELATED APPLICATIONS

This application is the U.S. national stage application of International Application PCT/JP2017/026043, filed Jul. 19, 2017, which international application was published on Apr. 5, 2018, as International Publication WO 2018/061419 in the Japanese language. The International Application claims priority of Japanese Patent Application No. 2016-194293, filed Sep. 30, 2016. The international application and Japanese application are both incorporated herein by reference, in entirety.

TECHNICAL FIELD

The present invention relates to a disposable wearing article having a stretchable structure in which an elastic film is sandwiched between a first sheet layer and a second sheet layer and a manufacturing method therefor.

BACKGROUND ART

In disposable wearing articles, for example, disposable diapers, in order to improve fitting to the body surface, it is common to impart elasticity to appropriate positions such as around the legs and around the waist. Conventionally, as a technique for imparting the elasticity, a technique of attaching elongated elastic members such as rubber threads in a state of being stretched in the longitudinal direction thereof has been widely adopted, but when it is desired to impart the elasticity with a certain range of width, a structure is adopted in which rubber threads are fixed in a state of being arranged side by side at intervals in the width direction. Further, as a material which is further excellent in surface fitting, a method of attaching the elastic film in a state of stretched in the direction of imparting the elasticity has also been proposed (refer to, for example, Patent Literature 1).

In a stretchable structure based on the elastic film (hereinafter also referred to as an elastic film stretchable structure), a stretchable region is formed by stacking an elastic film between a first sheet layer made of a nonwoven fabric and a second sheet layer made of a nonwoven fabric. In a state where the elastic film is stretched in the stretchable direction along surfaces of the first sheet layer, elastic film and the second sheet layer, the first sheet layer and the second sheet layer are bonded through bonding holes penetrating the elastic film at a number of dot-like sheet bonded portions arranged at intervals in a stretchable direction and a direction orthogonal to the stretchable direction. In such an elastic film stretchable structure, in a natural length state, as the elastic film contracts between the sheet bonded portions, intervals between the sheet bonded portions are decreased, and contraction wrinkles extending in a direction intersecting with the stretchable direction are formed between the sheet bonded portions in the first sheet layer and the second sheet layer. On the contrary, in a stretched state, as the elastic film is stretched between the sheet bonded portions, the intervals between the sheet bonded portions are increased and the contraction wrinkles in the first sheet layer and the second sheet layer are extended, and elastic stretching is allowed so that the first sheet layer and the second sheet layer can be completely spread. This elastic film stretchable structure has advantages as follows: surface fitting is excellent; the first sheet layer and the second sheet layer are not bonded to the elastic film and bonded each other but at an extremely low level, thus the elastic film stretchable structure has a satisfactory flexibility; and the bonding holes of the elastic film also contributes to improve air permeability in the thickness direction.

However, in the above-described conventional elastic film stretchable structure, the bonding holes surround the sheet bonded portion, and almost no air permeability can be expected except the periphery of the sheet bonded portion. In a disposable wearing article, it goes without saying that a decrease in air permeability brings discomfort due to stuffiness.

In such a viewpoint, as another embodiment, Patent Literature 1 proposes to form vent holes by tearing sheet bonded portions by pulling the elastic film stretchable structure in the direction orthogonal to the stretchable direction after forming the sheet bonded portions through welding. However, even in this case, the bonding holes are provided only at positions of the sheet bonded portions, and the improvement of the air permeability is limited by the arrangement and the number of the sheet bonded portions.

CITATION LIST

Patent Literature

Patent Literature 1: JP 2004-532758 A
Patent Literature 2: JP H09-285487 A
Patent Literature 3: JP 11-216163 A

SUMMARY OF INVENTION

Technical Problem

Therefore, the main object of the present invention is to improve air permeability without being restricted by sheet bonded portions in the elastic film stretchable structure.

Solution to Problem

The representative aspects of the present invention that have solved the above problems will be described below.

FIRST ASPECT

A disposable wearing article, having an elastic film stretchable structure in which an elastic film is stacked between a first sheet layer having air permeability and a second sheet layer having air permeability, the first sheet layer and the second sheet layer are bonded through bonding holes penetrating the elastic film or via the elastic film at a plurality of sheet bonded portions arranged at intervals, wherein a region having the elastic film stretchable structure includes a stretchable region that is stretchable in a stretchable direction, the stretchable region is contracted in the stretchable direction by a contraction force of the elastic film and is extensible in the stretchable direction, and vent holes are formed on the elastic film at sites where the elastic film does not overlap with the sheet bonded portions.

(Function and Effect)

In the present first aspect, since the vent holes are formed on the elastic film at the sites where the elastic film does not overlap with the sheet bonded portions, the air permeability can be improved without limitation from the sheet bonded portions.

SECOND ASPECT

The disposable wearing article according to claim 1, wherein each of the first sheet layer and the second sheet layer is a nonwoven fabric, the first sheet layer and the second sheet layer are bonded through the bonding holes penetrating the elastic film at the plurality of sheet bonded portions arranged at intervals, the first sheet layer and the second sheet layer are bonded to each other via a melted and solidified material of the elastic film in at least a part of the sheet bonded portion, and a dimension of the sheet bonded portion is larger than a dimension of the vent hole in at least one of the stretchable direction and a direction orthogonal to the stretchable direction in a state where the region having the elastic film stretchable structure is stretched to have elongation at an elastic limit in the stretchable direction (Function and Effect)

The bonding structure in which the first sheet layer and the second sheet layer, made of nonwoven fabrics, are bonded through the bonding holes at the sheet bonded portions and via the melted and solidified material of the elastic film, can be manufactured by performing simultaneously forming of the bonding holes on the elastic film and forming of the sheet bonded portions through welding as in the sixth aspect to be described later. When the first sheet layer and the second sheet layer are bonded via the melted and solidified material of the elastic film (as an adhesive) rather than are bonded to each other directly through the welding, the peel strength is increased. Here, when the size of the sheet bonded portion is smaller than the size of the vent hole, the position of the sheet bonded portion and the position of the vent hole may partially overlap. In such a case, the first sheet layer and the second sheet layer are directly bonded through the welding over the entire sheet bonded portion, and there is a possibility that the peel strength of the sheet bonded portion is lowered. When the sheet bonded portion is peeled off, the first sheet and the second sheet float at the peeled portion, and the appearance deteriorates.

On the other hand, in the case where the size of the sheet bonded portion is larger than the size of the vent hole as in the present aspect, at least a part of the sheet bonded portion is necessarily bonded via the melted and solidified material of the elastic film, and the peel strength is increased.

THIRD ASPECT

The disposable wearing article, according to claim 1 or 2, wherein each of the first sheet layer and the second sheet layer is a nonwoven fabric, the first sheet layer and the second sheet layer are bonded through the bonding holes formed on the elastic film at the plurality of sheet bonded portions arranged at intervals, the first sheet layer and the second sheet layer are bonded to each other via a melted and solidified material of the elastic film in at least a part of the sheet bonded portion, a dimension of the sheet bonded portion is smaller than a dimension of the vent hole, and a center-to-center interval of the two adjacent sheet bonded portions is larger than a center-to-center interval of the two adjacent vent holes in at least one of the stretchable direction and a direction orthogonal to the stretchable direction in a state where the region having the elastic film stretchable structure is stretched to have elongation at an elastic limit in the stretchable direction.

(Function and Effect)

The bonding structure in which the first sheet layer and the second sheet layer, made of nonwoven fabrics, are bonded through the bonding holes at the sheet bonded portions and via the melted and solidified material of the elastic film, can be manufactured by performing simultaneously forming of the bonding holes on the elastic film and forming of the sheet bonded portions through the welding as in the sixth aspect to be described later. When the first sheet layer and the second sheet layer are bonded via the melted and solidified material of the elastic film (as an adhesive) rather than are bonded to each other directly through the welding, the peel strength is increased. Here, when the size of the sheet bonded portion is smaller than the size of the vent hole, the position of the sheet bonded portion and the position of the vent hole may partially overlap. In such a case, the first sheet layer and the second sheet layer are directly bonded through the welding over the entire sheet bonded portion, and there is a possibility that the peel strength of the sheet bonded portion is lowered. When the sheet bonded portion is peeled off, the first sheet and the second sheet float at the peeled portion, and the appearance deteriorates.

Nevertheless, if the center-to-center interval of the two adjacent sheet bonded portions is larger than the center-to-center interval of the two adjacent vent holes as in this aspect, the probability is decreased that the position of the sheet bonded portion and the position of the vent hole overlap each other, and thus the peel strength hardly deteriorates.

FOURTH ASPECT

The disposable wearing article according to any one of claims 1 to 3, wherein the vent hole has a slit shape in a natural length state of the elastic film.

(Function and Effect)

The bonding structure in which the first sheet layer and the second sheet layer, made of nonwoven fabrics, are bonded through the bonding holes at the sheet bonded portions and via the melted and solidified material of the elastic film, can be manufactured by performing simultaneously forming of the bonding holes on the elastic film and forming of the sheet bonded portions through the welding as in the sixth aspect to be described later. When the first sheet layer and the second sheet layer are bonded via the melted and solidified material of the elastic film (as an adhesive) rather than are bonded to each other directly through the welding, the peel strength is increased. Here, if the size of the vent hole is large, the probability is increased that the first sheet layer and the second sheet layer are bonded directly through the welding at positions overlapping with the vent holes, and there is a possibility that the peel strength of the sheet bonded portion is lowered. When the sheet bonded portion is peeled off, the first sheet and the second sheet float at the peeled portion, and the appearance deteriorates.

On the other hand, by forming the slit-shaped vent holes as in the present aspect, the probability is decreased that the first sheet layer and the second sheet layer are bonded directly through the welding at positions overlapping with the vent holes, and even in the case where the first sheet layer and the second sheet layer are bonded directly through the welding, the welding area is reduced. Therefore, the peel strength of the first sheet layer and the second sheet layer hardly deteriorates.

In the case of a slit-shaped vent hole extending in a direction intersecting with the stretchable direction, the area of the vent hole is increased in a stretched state to improve the air permeability, whereas the probability is increased that the first sheet layer and the second sheet layer are bonded directly through the welding and thus the directly bonded area through the welding is increased. On the other hand, in the case of a slit-shaped vent hole extending in the stretchable direction, the area of the vent hole is not increased even in the stretched state, but the probability is decreased that the first sheet layer and the second sheet layer are bonded directly through the welding and thus the directly bonded area through the welding is remarkably decreased.

FIFTH ASPECT

The disposable wearing article according to any one of claims 1 to 4, wherein the disposable wearing article is an underpants type disposable wearing article including an outer member disposed in a front body and a back body provided as one unit or an outer member disposed in the front body and the back body provided separately, an inner member, which is attached to a center portion in a width direction of the outer member and provided to dispose from a front side of a crotch portion through the crotch portion to a back side of the crotch portion, side seal portions into which both side portions of the outer member in the front body and both side portions of the outer member in the back body are bonded respectively, a waist opening, and a pair of right and left leg openings, wherein the outer member in at least one of the front body and the back body is provided with the elastic film stretchable structure having a range in the width direction, which is corresponding to a distance between both the side seal portions and a range in a front-back direction, which is corresponding to at least a part of the side seal portion, so that the stretchable direction of the stretchable region is arranged in the width direction.

(Function and Effect)

An underpants type disposable wearing article is considered to be close to an underwear among disposable wearing article and it is common to provide a stretchable region in a broad range to ensure fitting. Therefore, the present invention is suitably applied for the stretchable region of such an underpants-type disposable wearing article.

SIXTH ASPECT

A manufacturing method of a disposable wearing article, including an elastic film stretchable structure in which an elastic film is stacked between a first sheet layer made of a nonwoven fabric and a second sheet layer made of a nonwoven fabric, and the first sheet layer and the second sheet layer are bonded through bonding holes penetrating the elastic film at a plurality of sheet bonded portions arranged at intervals, wherein a region having the elastic film stretchable structure includes a stretchable region that is stretchable in a stretchable direction, the stretchable region is contracted in the stretchable direction by a contraction force of the elastic film and is extensible in the stretchable direction, the method comprising when the region having the elastic film stretchable structure is formed, in a state where an elastic film having a plurality of vent holes arranged at intervals is sandwiched between the first sheet layer having air permeability and the second sheet layer having air permeability while the elastic film is stretched in the stretchable direction of the stretchable region, forming bonding holes on the elastic film by bonding the first sheet layer and the second sheet layer through welding at a plurality of positions arranged at intervals to melt the elastic film at the plurality of positions, and simultaneously bonding the first sheet layer and the second sheet layer by at least solidifying a melt material of the elastic film at the positions of the bonding holes.

(Function and Effect)

As described above, when the elastic film is sandwiched between the first sheet layer and the second sheet layer and the first sheet layer and the second sheet layer are bonded to each other directly through the welding by heat sealing, ultrasonic sealing or the like according to the arrangement pattern of the bonded portions, it is possible to perform simultaneously forming of the bonding holes on the elastic film and bonding of the first sheet layer and the second sheet layer through the bonding holes by solidifying the melt material of the elastic film and thus the manufacturing can be simply and efficiently carried out. In addition, since the elastic film has vent holes which are provided separately from the bonding holes, the air permeability can be improved without limitation from the arrangement and the number of the sheet bonded portions. Furthermore, since the first sheet layer and the second sheet layer are bonded via the melted and solidified material of the elastic film, high peel strength can be obtained.

Advantageous Effects of Invention

As described above, according to the present invention, in the elastic film stretchable structure, advantages such as being able to improve the air permeability without being restricted by the sheet bonded portions are provided.

BRIEF DESCRIPTION OF DRAWINGS

FIG. 12(a) is a schematic perspective view of an elastic film stretchable structure in a stretched state, and FIG. 12(b) is a schematic perspective view of the elastic film stretchable structure in a natural length state.

FIG. 17 is a cross-sectional view schematically illustrating a cross section of a main part of an outer member expanded to some extent.

FIG. 18 is a cross-sectional view schematically illustrating a cross section of a main part of an outer member expanded to some extent.

FIG. 19(a) is an enlarged plan view schematically illustrating a sheet bonded portion formed in a first welding mode, and FIG. 19(b) is an enlarged plan view schematically illustrating a sheet bonded portion formed in a third welding mode.

DESCRIPTION OF EMBODIMENTS

Figure 1:
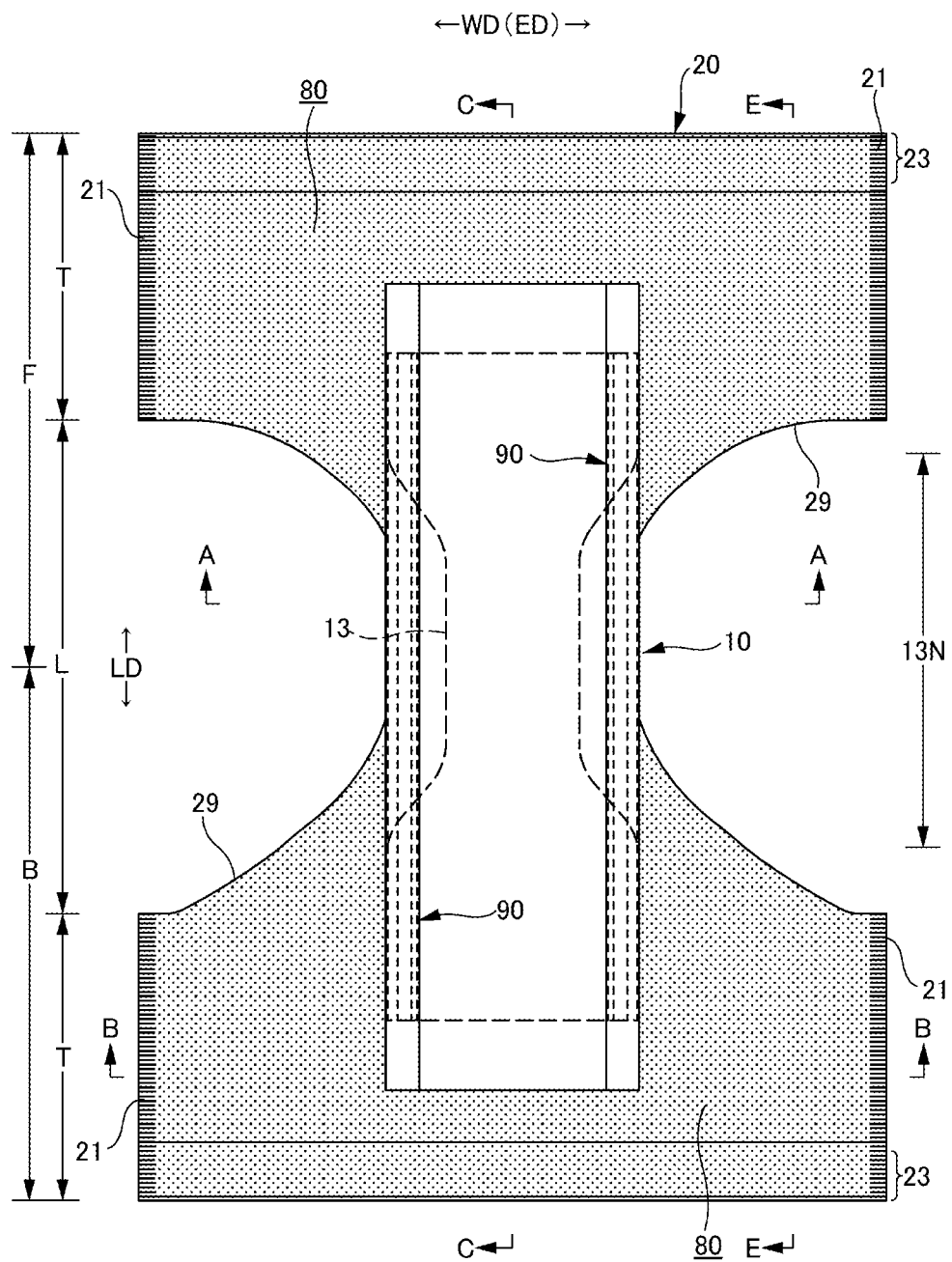
FIG. 1 is a plan view (internal surface side) of an underpants-type disposable diaper in a spread state.

Hereinafter, an embodiment of the present invention will be described in detail with reference to the accompanying drawings. In addition, a dotted portion in the cross-sectional view indicates a bonding means such as a hot melt adhesive.

FIGS. 1 to 6 illustrate an underpants-type disposable diaper. This underpants-type disposable diaper (hereinafter also simply referred to as a diaper) has an outer member 20 disposed in a front body F and a back body B, and an inner member 10 attached to an internal surface of the outer member 20, and the inner member 10 is formed by interposing an absorber 13 between a liquid pervious top sheet 11 and a liquid impervious sheet 12. Upon manufacturing, after a back surface of the inner member 10 is bonded to an internal surface (upper surface) of the outer member 20 by a bonding means such as a hot melt adhesive, the inner member 10 and the outer member 20 are folded at the center in the front-back direction LD (longitudinal direction) which is a boundary between the front body F and the back body B, and both side portions thereof are bonded to each other by heat sealing, a hot melt adhesive, or the like to form side seal portions 21. As a result, an underpants-type disposable diaper having a waist opening and a pair of left and right leg openings can be formed.

(Structure Example of Inner Member)

Figure 4:
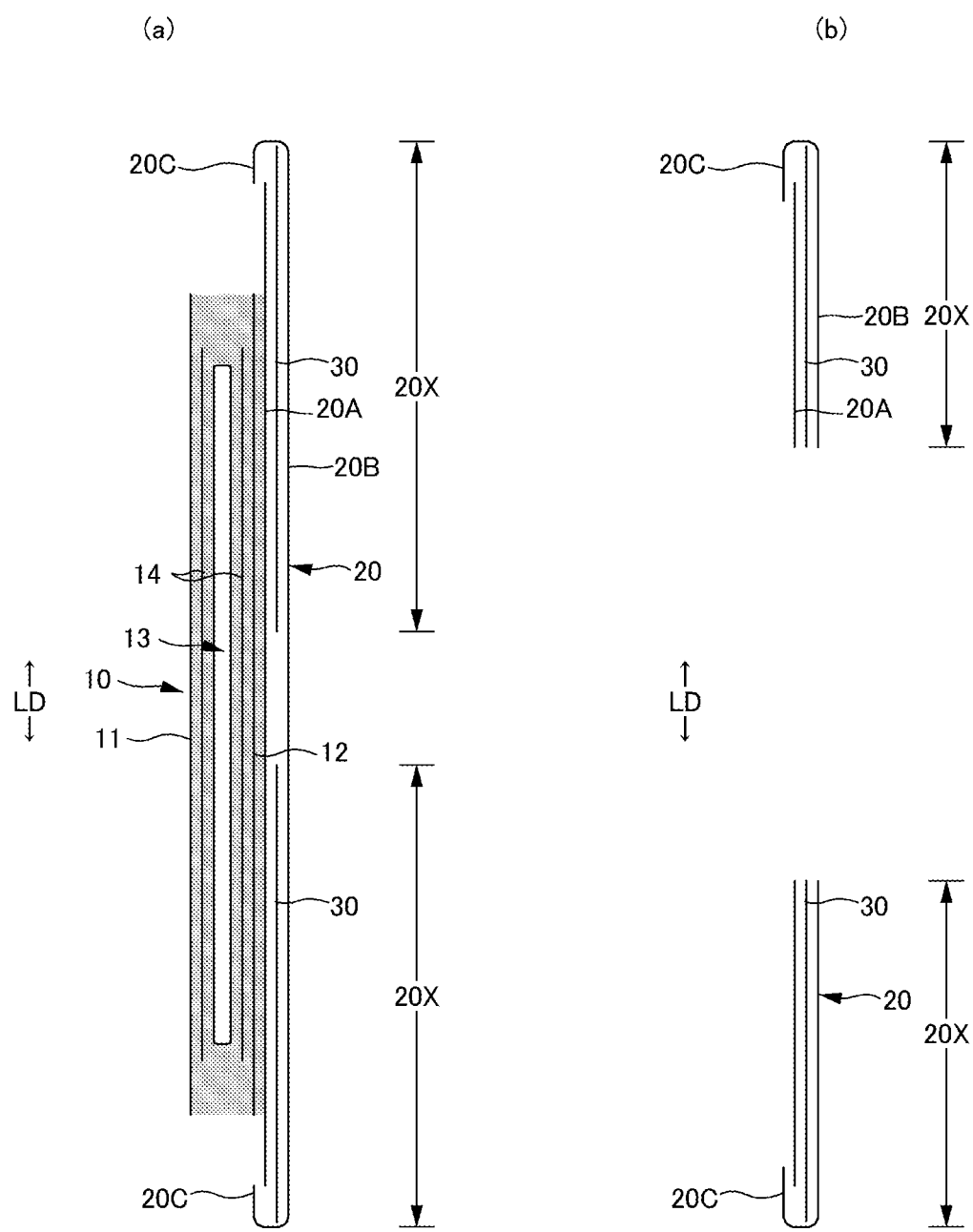
FIG. 4(a) is a cross-sectional view taken along line C-C of FIG. 1.
FIG. 4(b) is a cross-sectional view taken along line E-E of FIG. 1.
Figure 5:
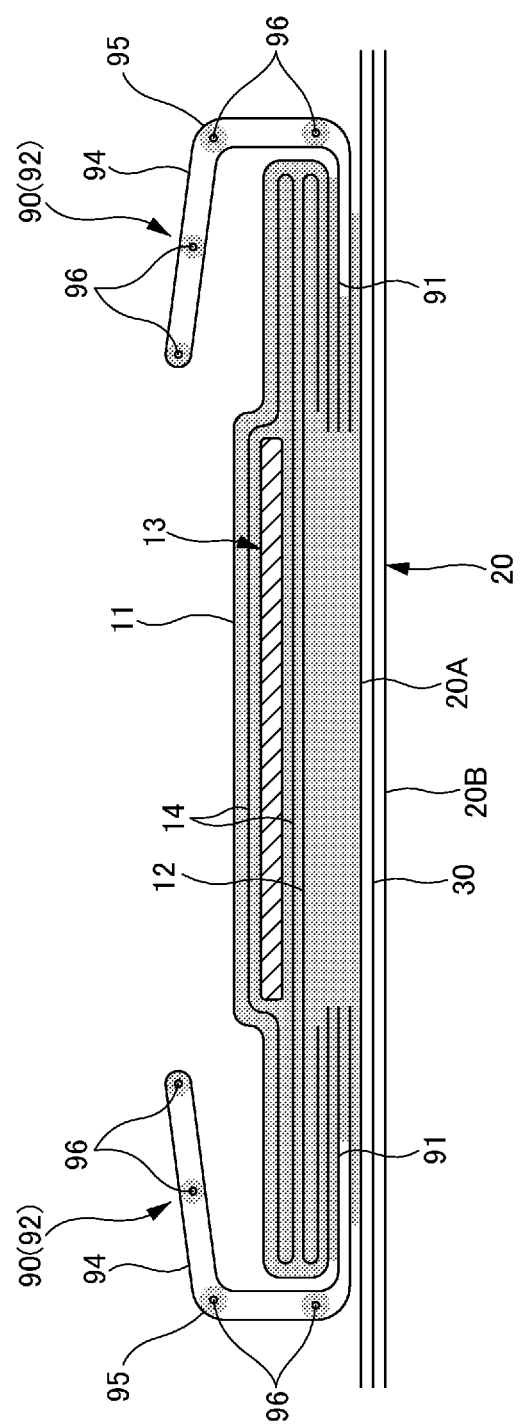
FIG. 5 is a cross-sectional view taken along line A-A of FIG. 1.
Figure 6:
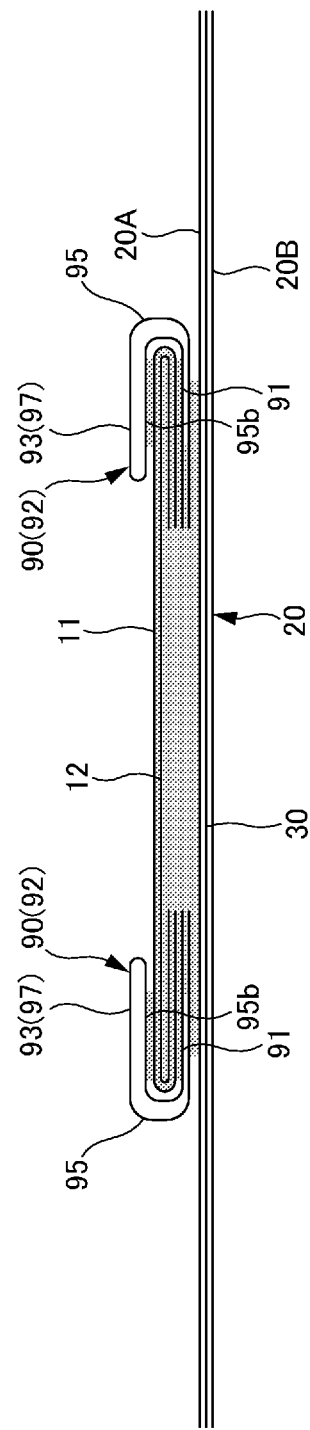
FIG. 6 is a cross-sectional view taken along line B-B of FIG. 1.

As illustrated in FIGS. 4 to 6, the inner member 10 has a structure in which the absorber 13 is interposed between the liquid pervious top sheet 11 and the liquid impervious sheet 12 made of polyethylene or the like to absorb and retain excreted fluid that has permeated through the liquid pervious top sheet 11. The planar shape of the inner member 10 is not particularly limited, but generally it is a substantially rectangular shape as illustrated in FIG. 1.

As the liquid pervious top sheet 11 covering a front surface side (skin side) of the absorber 13, a porous or non-porous nonwoven fabric, a porous plastic sheet, or the like is suitably used. For a raw material fiber forming a nonwoven fabric, in addition to synthetic fibers such as olefin type such as polyethylene or polypropylene, polyester type, polyamide type, etc., regenerated fibers such as rayon and cupra, and natural fibers such as cotton can be used, and a nonwoven fabric obtained by an appropriate processing method, such as a spun lace method, a spun bond method, a thermal bond method, a melt blown method, and a needle punch method can be used. In these processing methods, the spun lace method is excellent in terms of flexibility and drapability, and the thermal bond method is excellent in terms of bulkiness and softness. When a large number of through holes are formed on the liquid pervious top sheet 11, urine and the like are quickly absorbed, and dry touch property is excellent. The liquid pervious top sheet 11 extends to back surface sides of the absorber 13 by wrapping up side edge portions of the absorber 13.

For the liquid impervious sheet 12 covering a back surface side (non-skin contact side) of the absorber 13, a liquid impermeable plastic sheet such as polyethylene sheet or polypropylene sheet is used. In recent years, those having moisture permeability are preferably used from the viewpoint of prevention of stuffiness. This waterproof/moisture pervious sheet is a microporous sheet obtained by melt kneading an olefin resin such as polyethylene resin and polypropylene resin, and inorganic filler, forming a sheet with the kneaded materials, and then uniaxially or biaxially stretching the sheet.

The absorber 13 may be composed of a well-known basic component, for example, an accumulated body of pulp fibers, an assembly of filaments such as cellulose acetate, or nonwoven fabrics, and as necessary, super absorbent polymers can be mixed and fixed to the basic component. The absorber 13 can be wrapped with a wrapping sheet 14 having liquid permeability and liquid retention, such as crepe paper, to retain the shape and polymers, as required.

The shape of the absorber 13 is formed in a substantially hourglass shape having a narrowing portion 13N narrower than the front and back sides at a crotch portion. Although the size of the narrowing portion 13N can be determined as appropriate, the length in the front-back direction of the narrowing portion 13N can be set to about 20 to 50% of the maximum length of the diaper, and the width of the narrowest portion may be about 40 to 60% of the maximum width of the absorber 13. In the case where such a narrowing portion 13N is provided in the absorber, if the planar shape of the inner member 10 is substantially rectangular, the inner member 10 has free-absorber side portions 17 free of the absorber 13 according to the narrowing portion 13N of the absorber 13.

The liquid impervious sheet 12 is folded back to the back surface side together with the liquid pervious top sheet 11 on both sides in the width direction of the absorber 13. As this liquid impervious sheet 12, it is desirable to use an opaque sheet so that brown color of defecation, urine, and the like does not appear. As the opacification, a film obtained by internally adding a pigment or a filler such as calcium carbonate, titanium oxide, zinc oxide, white carbon, clay, talc, barium sulfate, or the like in a plastic is suitably used.

Three-dimensional gathers 90 fitting around the legs are formed on both sides of the inner member 10. As illustrated in FIGS. 5 and 6, the three-dimensional gather 90 includes a fixed portion 91, a main unit section 92, fallen portions 93, and a free portion 94. The fixed portion 91 is fixed to a side portion of a back surface of the inner member 10. The main unit section 92 extends from the fixed portion 91 through a side of the inner member 10 to above a side portion of a front surface of the inner member 10. The fallen portion 93 is formed by fixing the front and back end portions of the main unit section 92 to the side portion of the surface (the liquid pervious top sheet 11 in the illustrated form) of the inner member 10 in a fallen state. The free portion 94 is formed by non-fixing between the fallen portions 93. These portions are formed by folding a gather sheet 95 such as a nonwoven fabric sheet into a double sheet. The gather sheet 95 is attached to the entire front-back direction of the inner member 10, the fallen portions 93 are provided on a front side and a back side with respect to the free-absorber side portion 17, and the free portion 94 extends on both front and back sides of the free-absorber side portion 17. Further, between sheets of the double gather sheet 95, elongated elastic gather members 96 are disposed at a tip portion of the free portion and the like. As illustrated in FIG. 5, in a product state, the elastic gather member 96 is for making the free portion 94 stand up by an elastic contraction force.

In the embodiment illustrated in FIGS. 5 and 6, except the fallen non-stretchable portions 97, the elastic gather members 96 are adhered and fixed to the gather sheet 95 with a hot melt adhesive at positions of the elastic gather members 96, and opposing surfaces of the gather sheet 95 are bonded. In the fallen non-stretchable portion 97, no hot melt adhesive is provided at the positions of the elastic gather members 96, and therefore, the elastic gather members 96 and the gather sheet 95 are not adhered, and opposing surfaces of the gather sheet 95 are not bonded at the positions of the elastic gather members 96.

In the three-dimensional gather 90 illustrated in FIGS. 5 and 6, although the main unit section 92 is not folded back, any known structure can be used for the main unit section 92, as long as a character display 98 can be provided on the fallen non-stretchable portion 97 to be described later, such as a structure in which, a portion on a root side of the main unit section 92 obliquely stands toward the center in the width direction, and a portion on a tip side with respect to the center portion of the main unit section obliquely stands outward in the width direction.

As the elastic gather member 96, materials such as styrene rubber, olefin rubber, urethane rubber, ester rubber, polyurethane, polyethylene, polystyrene, styrene butadiene, silicone, polyester, and the like which are usually used can be used. Further, in order to make it difficult to be seen from the outside, it is better that the fineness is set to 925 dtex or less, the tension is set to 150 to 350%, and the interval is set to 7.0 mm or less. As the elastic gather member 96, in addition to a thread-like shape as the illustrated embodiment, a tape-shaped member having a certain width can be used.

Like the liquid pervious top sheet 11, for a raw material fiber forming the above-described gather sheet 95, in addition to synthetic fibers such as olefin type such as polyethylene or polypropylene, polyester type, amide type, etc., regenerated fibers such as rayon and cupra, and natural fibers such as cotton can be used, and a nonwoven fabric obtained by an appropriate processing method, such as a spun bond method, a thermal bond method, an melt blown method, and a needle punch method can be used. In particular, to prevent stuffiness, nonwoven fabric having low basis weight and excellent in air permeability is preferably used. Further, with respect to the gather sheet 95, in order to prevent permeation of urine or the like and also to prevent irritation and improve the texture to the skin (dryness), it is desirable to use a water repellent treated nonwoven fabric coated with silicone type, paraffin metal type, or alkyl chromic chloride type water repellent, etc.

As illustrated in FIGS. 3 to 6, a back surface of the inner member 10 is bonded to an internal surface of the outer member 20 with a hot melt adhesive or the like in an inner and outer fixed region 10B (shaded region). The inner and outer fixed region 10B can be determined appropriately and can be substantially the whole part in the width direction WD of the inner member 10. However, it is preferable that the both end portions in the width direction of the inner and outer fixed region are not fixed to the outer member 20.

(Structure Example of Outer Member)

Figure 7:
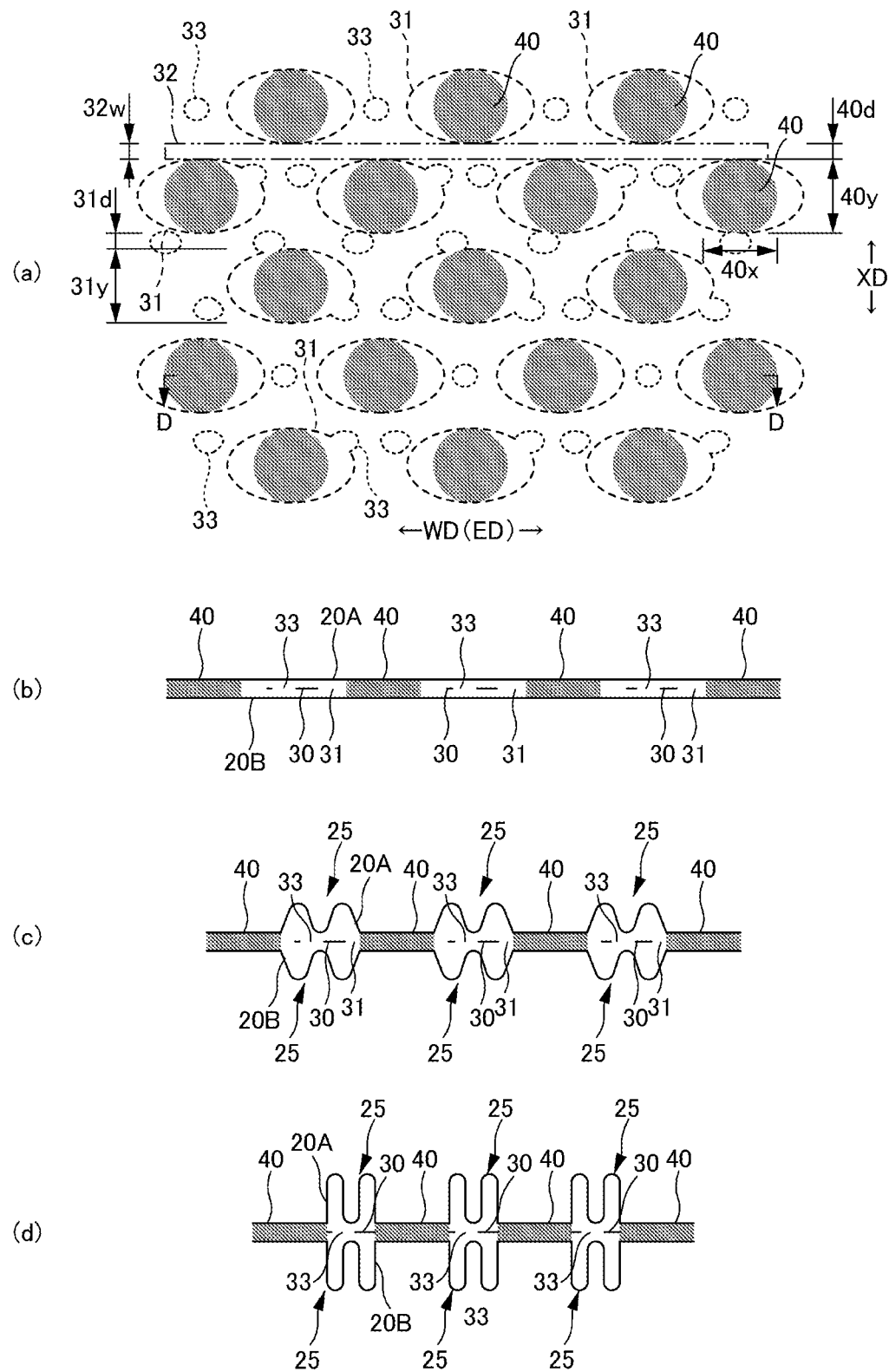
FIG. 7(a) is a plan view of a main part of a stretchable region.
FIG. 7(b) is a cross-sectional view taken along line D-D of FIG. 7(a)
FIG. 7(c) is a cross-sectional view in a worn state.
FIG. 7(d) is a cross-sectional view in a natural length state.

The outer member 20 extends from a side edge to a lateral side of the absorber 13. In the crotch portion, the side edges of the outer member 20 may be located closer to a center side than side edges of the inner member 10 in the width direction as in the illustrated embodiment, or may be located closer to the outer sides than the side edges of the inner member 10 in the width direction. Further, the outer member 20 includes a lower torso portion T corresponding to a range in the front-back direction of each side seal portion 21, and an intermediate portion L corresponding to a range in the front-back direction between the lower torso portion T of the front body F and the lower torso portion T of the back body B. In the outer member 20 of the illustrated embodiment, except for the middle in the front-back direction of the intermediate portion L, as illustrated in FIGS. 2 and 4 to 6, an elastic film 30 is stacked between a first sheet layer 20A and a second sheet layer 20B, and as illustrated in FIG. 7, the outer member 20 has an elastic film stretchable structure 20X in which the first sheet layer 20A and the second sheet layer 20B are bonded through the bonding holes 31 penetrating the elastic film 30 at a large number of sheet bonded portions 40 arranged at intervals, and a stretchable direction ED is along the width direction WD. The first sheet layer 20A and the second sheet layer 20B may be indirectly bonded via the elastic film 30, not through the bonding holes 31 of the elastic film 30. The planar shape of the outer member 20 is formed by recessed leg lines 29 so as to form leg openings at both side edges in the width direction of the intermediate portion L and has a shape resembling an hourglass as a whole. The outer member 20 may be divided into the front body F and the back body B and may be arranged so that those are spaced apart from each other in the front-back direction LD at the crotch portion.

Figure 2:
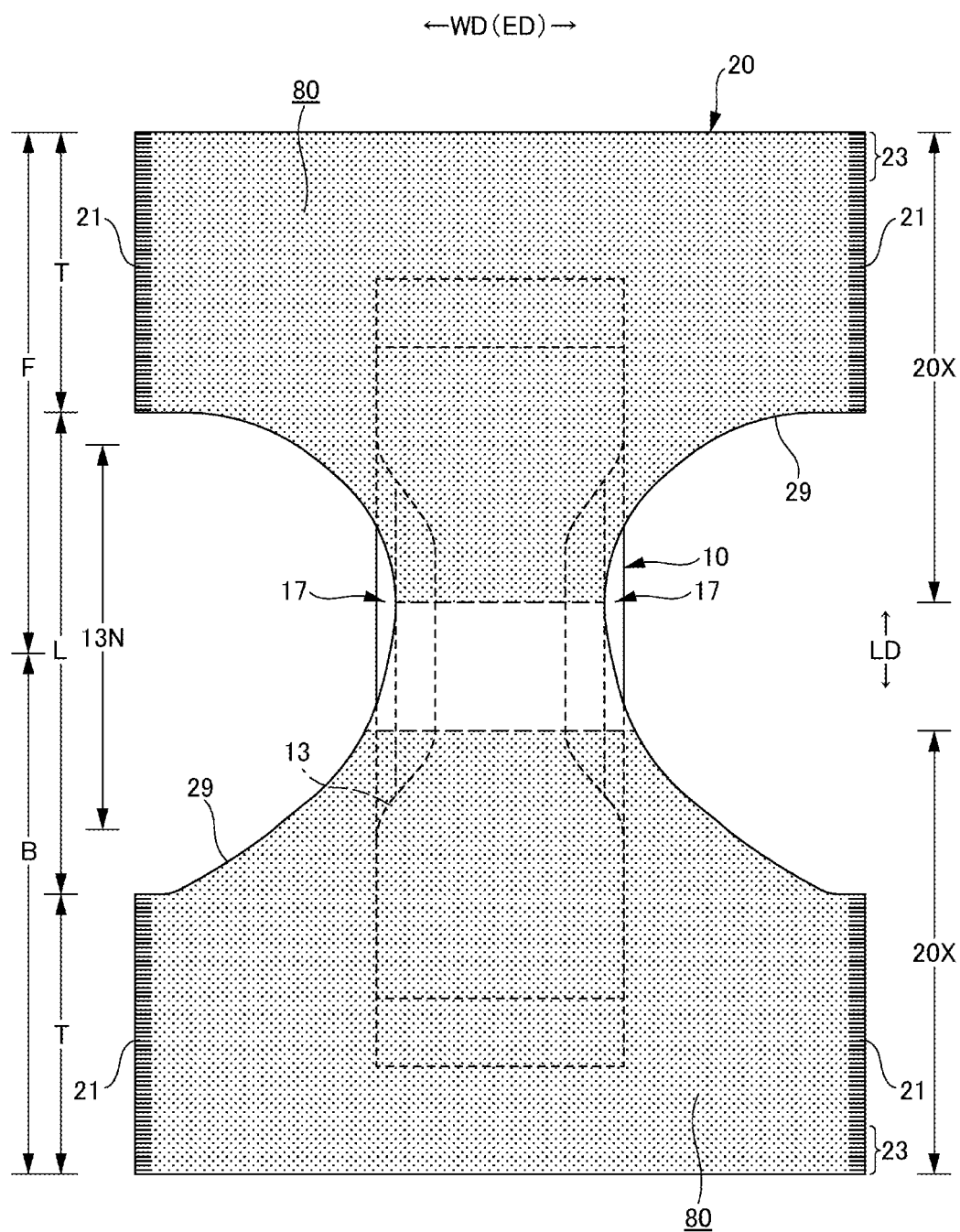
FIG. 2 is a plan view (external surface side) of the underpants-type disposable diaper in the spread state.
Figure 3:
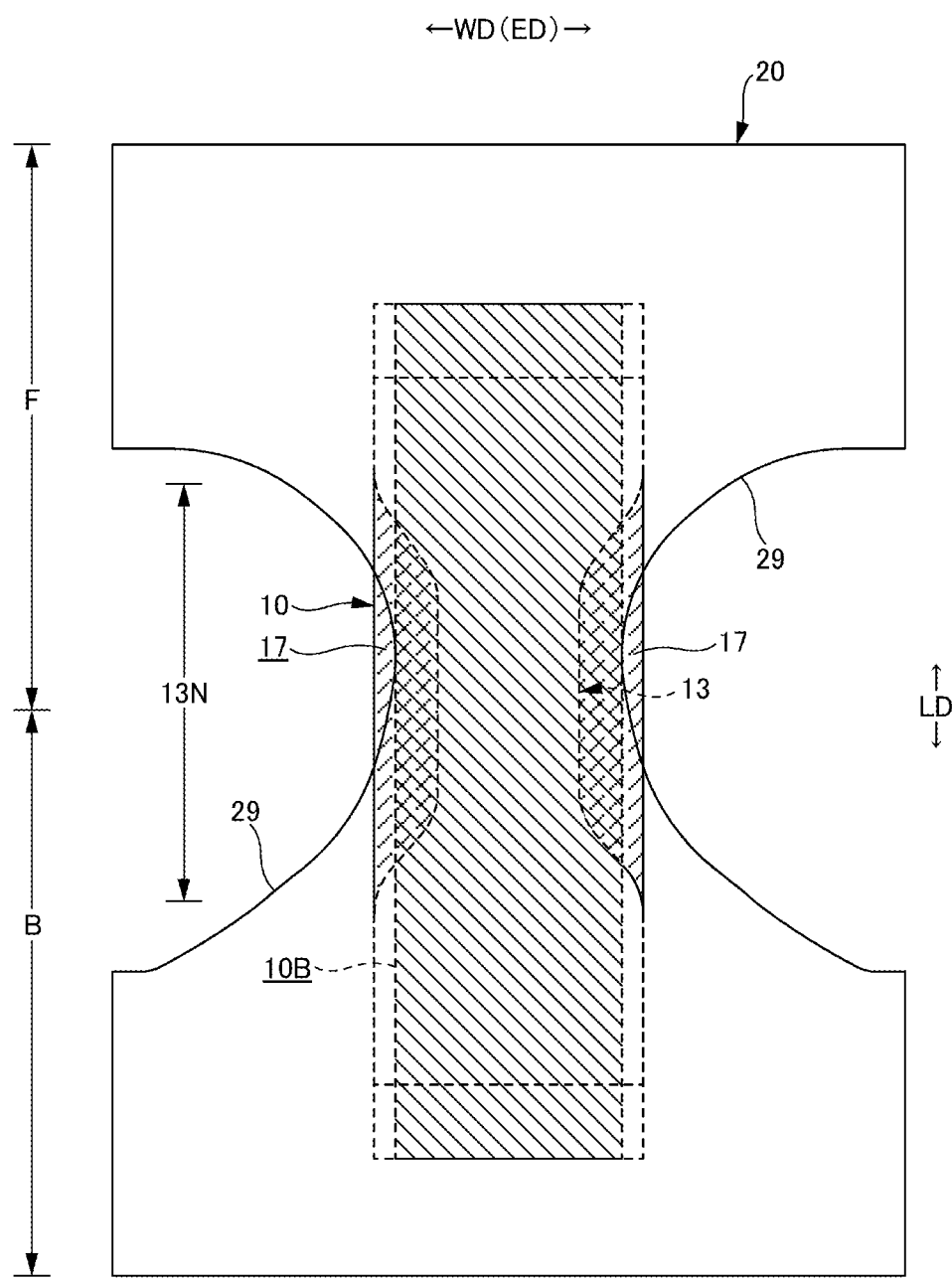
FIG. 3 is a plan view illustrating only a main part of the underpants-type disposable diaper in the spread state.

In the embodiment illustrated in FIGS. 1 and 2, the elastic film stretchable structure 20X extends to a waist portion 23. When the elastic film stretchable structure 20X is used in the waist portion 23, for example, tightening of the waist portion 23 may be insufficient. Therefore, as illustrated FIGS. 15 and 16, without providing the elastic film stretchable structure 20X in the waist portion 23, a stretchable structure by conventional elongated waist elastic members 24 can be provided if necessary. The waist elastic members 24 are elongated elastic members such as a plurality of rubber threads arranged at intervals in the front-back direction LD and provide a stretching force so as to tighten around the waist of a wearer. The waist elastic members 24 are not arranged substantially as a single bundle with a close spacing, but three or more, preferably five or more waist elastic members 24 are disposed at intervals of about 3 to 8 mm so as to form a predetermined stretchable zone. A stretch rate at the time of fixing the waist elastic member 24 can be appropriately determined, but it can be set to about 230 to 320% for normal adult use. Although a rubber thread is used for the waist elastic member 24 in the illustrated example, another elongated elastic member such as flat rubber or the like may be used. Although not illustrated, it is also possible to provide the elastic film 30 in the waist portion 23 and to provide the elongated waist elastic members 24 at positions overlapping with the elastic film 30 so as to have a stretchable structure with elasticity by the both of the elastic film and the elongated waist elastic members. Also, in the illustrated embodiment, the elongated elastic members extending along the leg openings are not provided at the edge portions of the leg openings of the outer member 20. However in these edge portions, the elongated elastic members may be provided at a portion overlapping with the elastic film 30 or the elongated elastic members may be provided in place of the elastic film 30.

In another mode, although not illustrated, appropriate modification is possible such that the elastic film stretchable structure 20X is not provided in the intermediate portion L between the lower torso portion T of the front body F and the lower torso portion T of the back body B, the stretchable structure 20X is continuously provided in the front-back direction LD from the inside of the lower torso portion T of the front body F to the inside of the lower torso portion T of the back body B through the intermediate portion L, or the elastic film stretchable structure 20X is provided only on any one of the front body F and the back body B.

Figure 8:
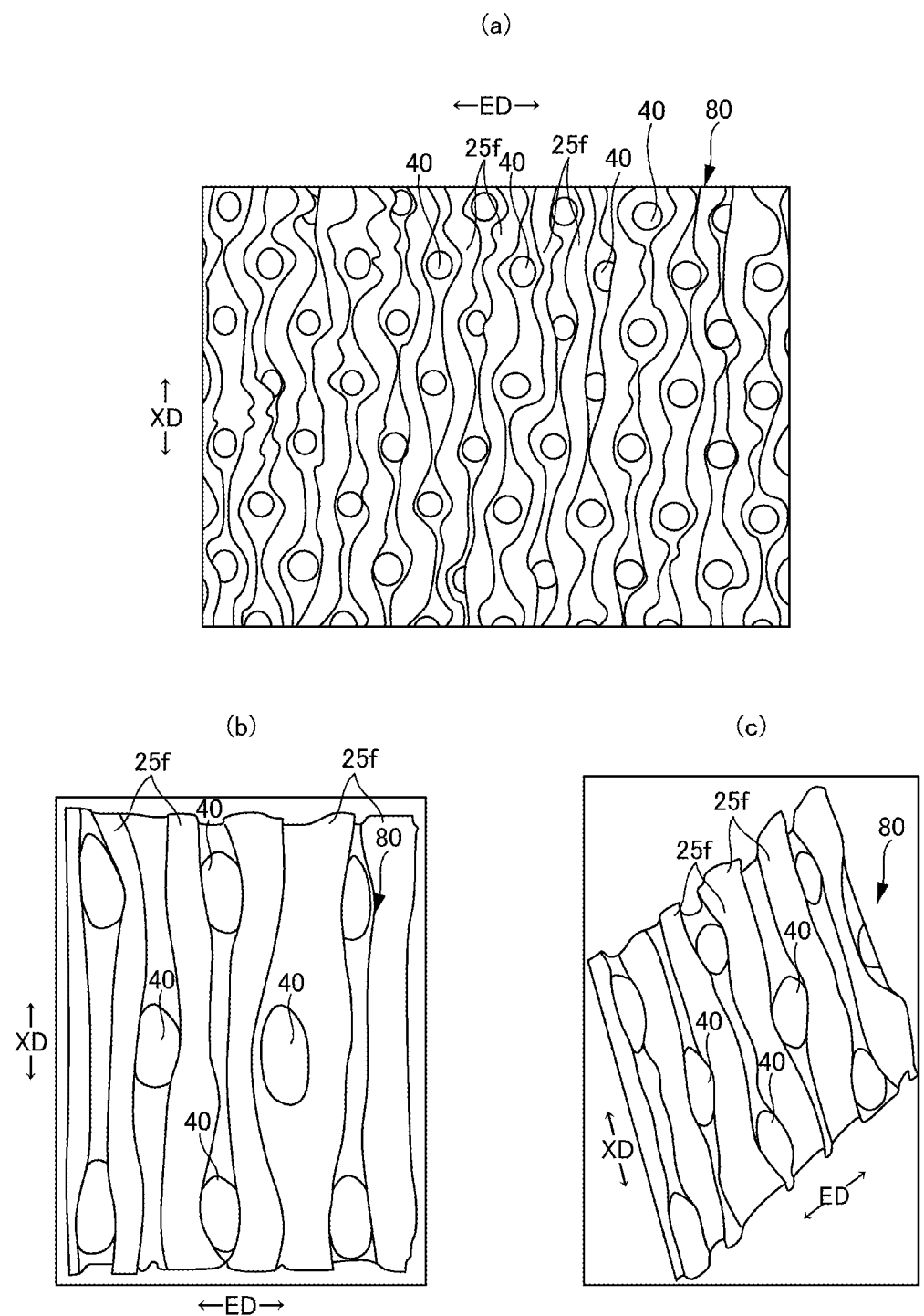
FIG. 8(a) is a plan view of a stretchable region.
FIG. 8(b) is an enlarged plan view of the stretchable region.
FIG. 8(c) is an enlarged perspective view of the stretchable region.
Figure 9:
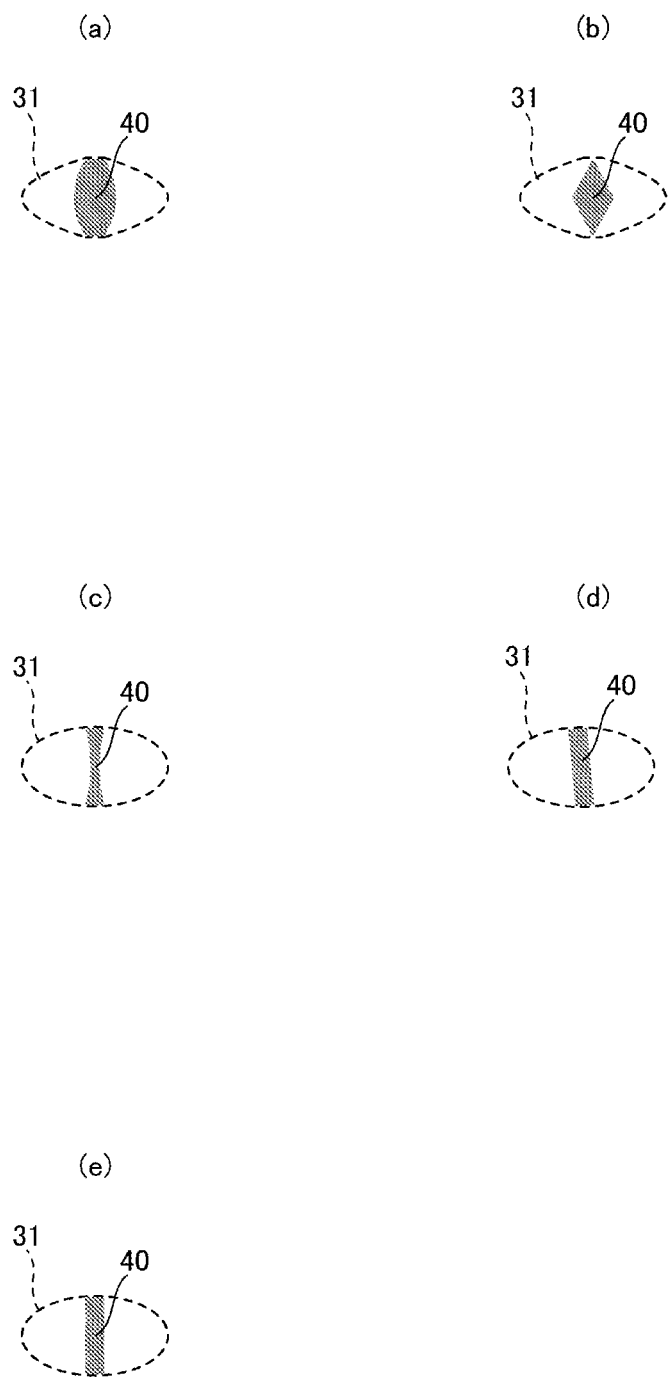
FIG. 9 is an enlarged plan view of a main part of a sheet bonded portion.
Figure 13:
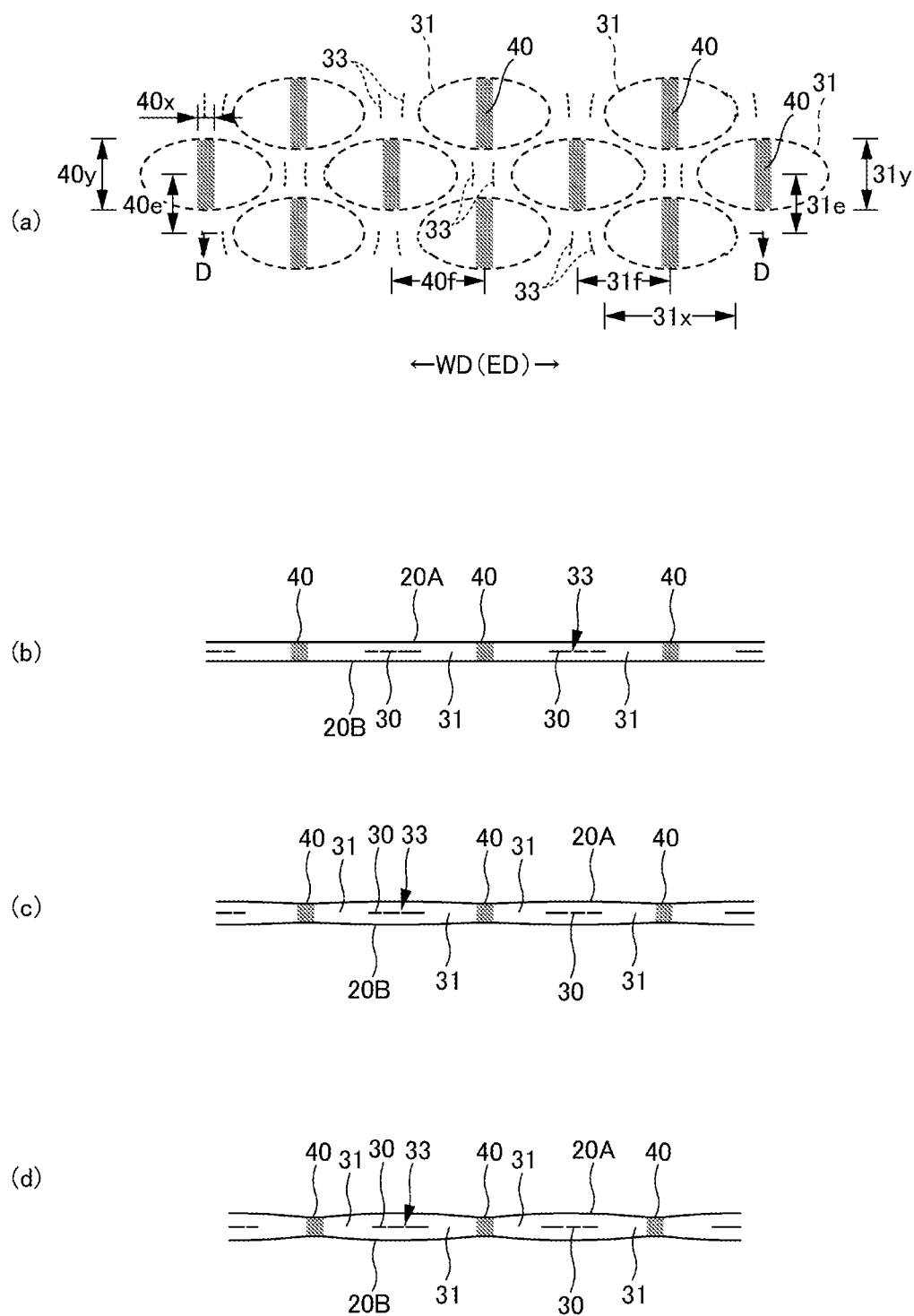
FIG. 13(a) is a plan view of a main part of a non-stretchable region.
FIG. 13(b) is a cross-sectional view taken along line D-D of FIG. 13(a)
FIG. 13(c) is a cross-sectional view in a worn state.
FIG. 13(d) is a cross-sectional view in a natural length state.

Although the shape of the sheet bonded portion 40 and the shape of the bonding hole 31 in a natural length state can be determined as appropriate, it can be an arbitrary shape such as a perfect circle (refer to FIGS. 7 and 8), an ellipse, a polygon such as a triangle, a rectangle (refer to FIGS. 9(e) and 13), and a rhombus (refer to FIG. 9(b)), or a convex lens shape (refer to FIG. 9(a)), a concave lens shape (refer to FIG. 9(c)), a star shape, a cloud shape, and the like. Although the size of the sheet bonded portion is not particularly limited, the maximum length (dimension in the direction orthogonal to the stretchable direction) 40y is preferably 0.5 to 3.0 mm, particularly preferably 0.7 to 1.1 mm, and the maximum width (dimension in the stretchable direction) 40x is preferably 0.1 to 3.0 mm, particularly preferably 0.1 to 1.1 mm in the case where the shape is long in the direction XD orthogonal to the stretchable direction.

The size of the sheet bonded portion 40 may be determined appropriately, but if the size is too large, the hardness of the sheet bonded portion 40 exerts an influence on the touch, and if it is too small, a bonded area is small, and materials are insufficiently adhered to each other. Therefore, in the usual case, the area of the sheet bonded portion 40 is preferably about 0.14 to 3.5 mm². The area of an opening of the bonding hole 31 may be equal to or greater than that of the sheet bonded portion because the sheet bonded portion is formed through the bonding hole 31, and the area is preferably set to about 1 to 1.5 times the area of the sheet bonded portion. The area of the opening of the bonding hole 31 means a value in a state where the elastic film 30, the first sheet layer 20A and the second sheet layer 20B are provided in one unit, not in a state of the elastic film 30 alone, and in a state of natural length and means the minimum value in the case where the area of the opening of the bonding hole 31 is not uniform in the thickness direction like that the area is different between the front and back of the elastic film 30.

Figure 21:
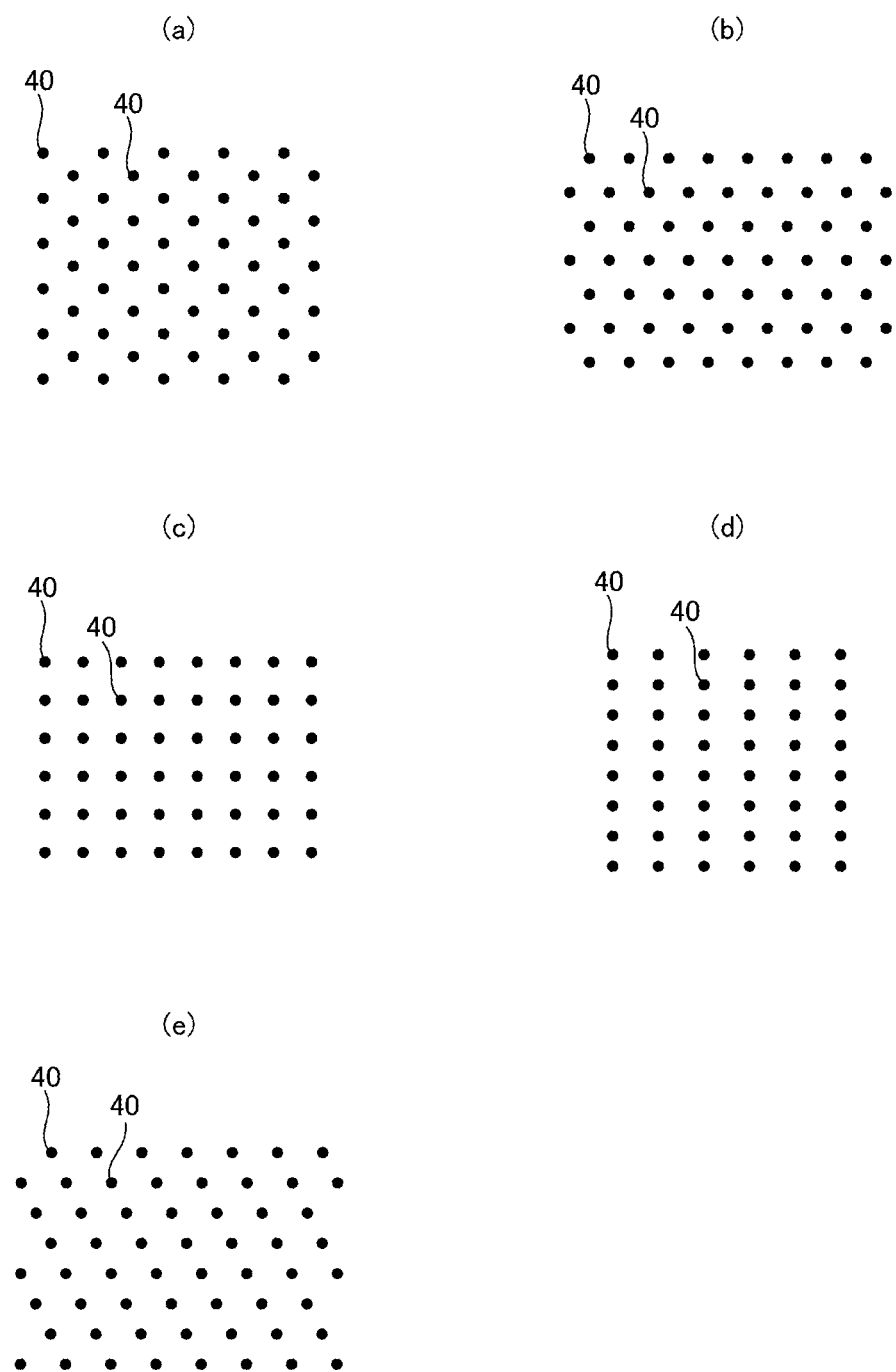
FIG. 21 is a plan view illustrating various arrangement examples of sheet bonded portions.

Although the planar arrangement of the sheet bonded portions 40 and the bonding holes 31 can be appropriately determined, it is preferable to adopt a planar arrangement in which the sheet bonded portions 40 and the bonding holes 31 are regularly repeated, such as an oblique lattice shape as illustrated in FIG. 21(a), a hexagonal lattice shape (also referred to as a staggered lattice shape) as illustrated in FIG. 21(b), a square lattice shape as illustrated in FIG. 21(c), a rectangular lattice shape as illustrated in FIG. 21(d), and a parallelotope lattice shape as illustrated in FIG. 21(e) (a mode in which two groups are provided so that a large number of parallel oblique row groups intersect each other, as shown in the drawings), etc. (including a mode in which these shapes are inclined at an angle of less than 90° with respect to the stretchable direction ED). Additionally, it is also possible to adopt a planar arrangement in which a group of the sheet bonded portions 40 (arrangement of the group may be regular or irregular, and a pattern, a letter shape, etc. may be used) is regularly repeated.

The first sheet layer 20A and the second sheet layer 20B are bonded at the sheet bonded portions 40 through the bonding holes 31 formed on the elastic film 30. In this case, it is desirable that neither the first sheet layer 20A nor the second sheet layer 20B is bonded to the elastic film 30 at least in a portion other than a portion between the first sheet layer 20A and the second sheet layer 20B in the sheet bonded portion 40.

Means for bonding the first sheet layer 20A and the second sheet layer 20B at the sheet bonded portion 40 is not particularly limited. For example, in the sheet bonded portion 40, the first sheet layer 20A and the second sheet layer 20B may be bonded with a hot melt adhesive or may be bonded by means of material welding such as heat sealing or ultrasonic sealing.

In the case where the first sheet layer 20A and the second sheet layer 20B are bonded through the bonding hole 31 of the elastic film 30 at the sheet bonded portion 40, as a mode in which the sheet bonded portions 40 are formed by material welding, it is possible to adopt any one of a first welding mode, a second welding mode, and a third welding mode. In the first welding mode, the first sheet layer 20A and the second sheet layer 20B are bonded only by a melted and solidified material 20m corresponding to a most part of or a part of at least one of the first sheet layer 20A and the second sheet layer 20B in the sheet bonded portion 40 (refer to FIG. 17(a)). In the second welding mode, the first sheet layer 20A and the second sheet layer 20B are bonded only by a melted and solidified material 30m corresponding to the whole of, the most part of, or a part of the elastic film 30 in the sheet bonded portion 40 (refer to FIG. 17(b)). In the third welding mode, the first welding mode and the second welding mode are combined (refer to FIG. 17(c)). However, the second welding mode and the third welding mode are preferable. In particular, a mode is preferable in which the first sheet layer 20A and the second sheet layer 20B are bonded by the melted and solidified material 20m corresponding to a part of the first sheet layer 20A and the second sheet layer 20B and the melted and solidified material 30m of the whole of or most of the elastic film 30 in the sheet bonded portion 40. In the third welding mode illustrated in FIG. 19(b), the melted and solidified material 30m of the elastic film 30 represented by white is found in the melted and solidified materials 20m with the fibers of the first sheet layer 20A or the second sheet layer 20B represented in black. However, in the first welding mode illustrated in FIG. 19(a), the melted and solidified material of the elastic film is not seen in the melted and solidified material 20m of fibers of the first sheet layer 20A or the second sheet layer 20B.

As in the first bonding mode and the third bonding mode, when the first sheet layer 20A and the second sheet layer 20B are bonded by the melted and solidified material 20m corresponding to a most part of or a part of at least one of the first sheet layer 20A and the second sheet layer 20B as an adhesive, it is preferable that a part of the first sheet layer 20A and the second sheet layer 20B is not melted in order not to harden the sheet bonded portion 40. When the first sheet layer 20A and the second sheet layer 20B are nonwoven fabrics, a case in which a part of the first sheet layer 20A and the second sheet layer 20B is not melted includes a mode in which for all fibers of the sheet bonded portion 40, a core (including not only a core of a conjugate fiber but also a central portion of a single component fiber) remains while a surrounding portion (including not only a sheath in a conjugate fiber but also a portion on a surface layer side of a single component fiber) is melted, and a mode in which some fibers do not melt at all, but all remaining fibers melt or a core remains but a surrounding portion melts in each of the remaining fibers.

When the first sheet layer 20A and the second sheet layer 20B are bonded using the melted and solidified material 30m of the elastic film 30 as an adhesive like the second welding mode and the third welding mode, the peel strength becomes high. In the second welding mode, under the condition that a melting point of at least one of the first sheet layer 20A and the second sheet layer 20B is higher than the melting point of the elastic film 30 and a heating temperature at the time of forming the sheet bonded portion 40, the elastic film 30 is sandwiched between the first sheet layer 20A and the second sheet layer 20B, and a portion to be the sheet bonded portion 40 is pressurized and heated so that only the elastic film 30 is melted, thereby performing manufacture. On the other hand, in the third welding mode, under the condition that a melting point of at least one of the first sheet layer 20A and the second sheet layer 20B is higher than the melting point of the elastic film 30, the elastic film 30 is sandwiched between the first sheet layer 20A and the second sheet layer 20B, and portion to be the sheet bonded portion 40 is pressurized and heated so that at least one of the first sheet layer 20A and the second sheet layer 20B and the elastic film 30 is melted, thereby performing manufacture. From such a viewpoint, the melting point of the elastic film 30 is preferably about 80 to 145° C., and the melting points of the first sheet layer 20A and the second sheet layer 20B are preferably about 85 to 190° C., particularly preferably 150 to 190° C. The difference between the melting points of the first sheet layer 20A and the second sheet layer 20B and the melting point of the elastic film 30 is preferably about 60 to 90° C. The heating temperature is preferably about 100 to 150° C.

In the second welding mode and the third welding mode, when the first sheet layer 20A and the second sheet layer 20B are nonwoven fabrics, the melted and solidified material 30m of the elastic film 30 may infiltrate among fibers throughout the entire thickness direction of the first sheet layer 20A and the second sheet layer 20B in the sheet bonded portion 40 as illustrated in FIG. 18(c). However, as illustrated in FIGS. 17(b) and 17(c) and 18(a), in a mode in which the melted and solidified material 30m infiltrates among fibers in the thickness direction halfway or as illustrated in FIG. 18(b), in a mode in which the melted and solidified material 30m hardly infiltrates among the fibers of the first sheet layer 20A and the second sheet layer 20B, the flexibility of the sheet bonded portion 40 is further improved.

Figure 20:
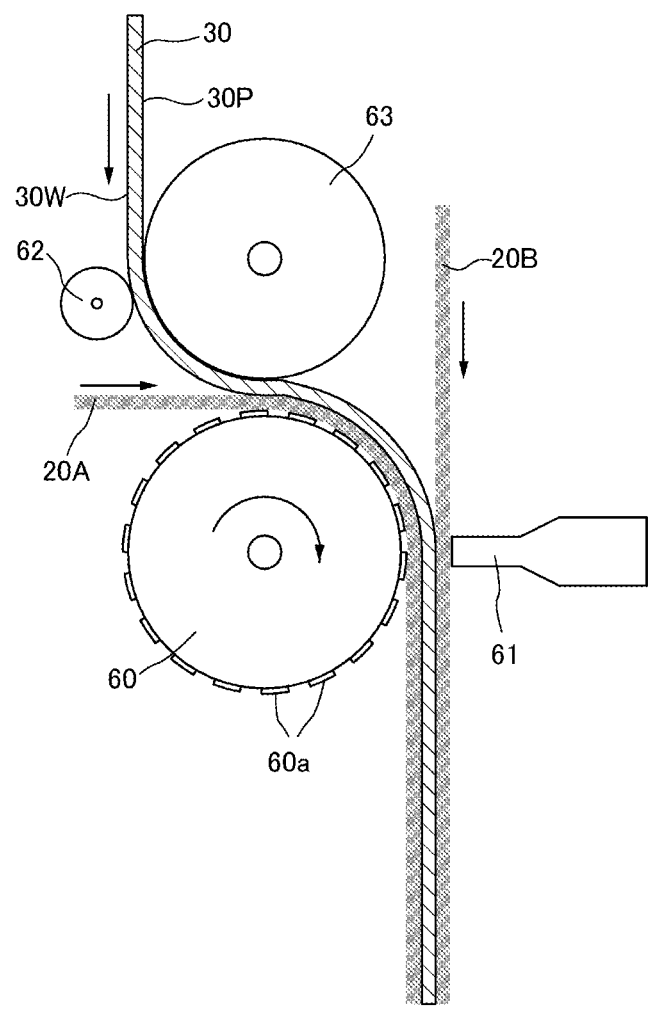
FIG. 20 is a schematic diagram of an ultrasonic sealing device.

FIG. 20 shows an example of an ultrasonic sealing device suitable for forming the second welding mode and the third welding mode. In this ultrasonic sealing device, to form sheet bonded portions 40, the first sheet layer 20A, the elastic film 30, and the second sheet layer 20B are fed between an ultrasonic horn 61 and an anvil roll 60 having protruding portions 60a formed in a pattern of the sheet bonded portions 40 on an external surface for forming the sheet bonded portions 40. In this instance, for example, when a feed speed of conveyance of the elastic film 30 at an upstream side by a feed drive roll 63 and a nip roll 62 is controlled to be lower than a feed speed of conveyance after the anvil roll 60 and the ultrasonic horn 61, the elastic film 30 is stretched to a predetermined stretch rate in the MD direction (machine direction, flow direction) on a path from a nip position by the feed drive roll 63 and the nip roll 62 to a sealing position by the anvil roll 60 and the ultrasonic horn 61. The stretch rate of the elastic film 30 can be set by selecting a speed difference between the anvil roll 60 and the feed drive roll 63 and can be set to, for example, about 300% to 500%. The reference sign 62 denotes the nip roll. The first sheet layer 20A, the elastic film 30, and the second sheet layer 20B, which are fed between the anvil roll 60 and the ultrasonic horn 61, are in a stacked state in this order, and while being pressurized between the protruding portions 60a and the ultrasonic horn 61, are heated by ultrasonic vibration energy of the ultrasonic horn 61. The bonding holes 31 are formed on the elastic film 30 by melting only the elastic film 30 or melting the elastic film 30 and at least one of the first sheet layer 20A and the second sheet layer 20B, and simultaneously the first sheet layer 20A and the second sheet layer 20B are bonded through the bonding holes 31. Therefore, in this case, by selecting the size, shape, separation distance, arrangement pattern in the roll length direction and roll circumferential direction, etc. of the protruding portion 60a of the anvil roll 60, the area rate of the sheet bonded portions 40 can be selected.

The reason why the bonding hole 31 is formed is not necessarily clear, but it is considered that openings are formed by melting the elastic film 30 at portions corresponding to the protruding portions 60a of the anvil roll 60 so as to be removed from the surroundings. At this time, as illustrated in FIGS. 7(a) and 13(a), a portion between two adjacent bonding holes 31 aligned in the stretchable direction ED in the elastic film 30 is cut at both sides thereof in the stretchable direction by the bonding holes 31, and loses support at both sides in a contraction direction. Therefore, within an extent that continuity in the orthogonal direction XD can be maintained, the closer to the central side in the direction XD orthogonal to the contraction direction, the more the elastic film 30 contracts to the central side in the stretchable direction ED to be commensurable so that the bonding-holes 31 are stretched in the stretchable direction ED. Then, when the sheet bonded portions 40 are formed in a pattern with sections being left in which the elastic film 30 linearly continues along the stretchable direction ED like a stretchable region 80 to be described later, as illustrated in FIG. 7(a), when the elastic film 30 contracts to a natural length state for example by cutting for obtaining individual products, stretched portions of the bonding hole 31 contract in the stretchable direction ED so that gaps cannot be formed between the bonding hole 31 and the sheet bonded portion 40. On the other hand, when the sheet bonded portions 40 are formed in a pattern without such sections in which the elastic film 30 linearly continues along the stretchable direction ED like a non-stretchable region 70 to be described later, as illustrated in FIG. 13(*a*), even if the elastic film 30 is cut for obtaining the individual products, contraction is not substantially performed. Therefore, large gaps are left between the bonding hole 31 and the sheet bonded portion 40.

The constituent materials of the first sheet layer 20A and the second sheet layer 20B are not particularly limited as long as they have sheet shapes, but it is preferable to use a nonwoven fabric from the viewpoints of air permeability and flexibility. In the nonwoven fabric, a raw material fiber thereof is not particularly limited. Examples of the raw material fiber can include synthetic fibers such as olefin type such as polyethylene and polypropylene, polyester type, and polyamide type, regenerated fibers such as rayon and cupra, natural fibers such as cotton, blend or conjugate fibers in which two or more of these fibers are used. Further, the nonwoven fabric may be manufactured by any process. Examples of the processing method include known methods such as a spun lace method, a spunbond method, a thermal bond method, a melt blown method, a needle punch method, an air-through method, and a point bond method. When a nonwoven fabric is used, its basis weight is preferably about 10 to 25 g/m$^2$. Further, a part or the whole of the first sheet layer 20A and the second sheet layer 20B may be a pair of layers in which a single material is folded back to face each other. For example, as in the illustrated embodiment, in the waist portion 23, the constituent material located on the outer side is the second sheet layer 20B, and the folded portion 20C folded back to the internal surface side at a waist opening edge is the first sheet layer 20A, and the elastic film 30 is interposed therebetween. In the rest part, the constituent material located on the inner side is the first sheet layer 20A, the constituent material located on the outer side is the second sheet layer 20B, and the elastic film 30 can be interposed therebetween. It is obvious that the constituent material of the first sheet layer 20A and the constituent material of the second sheet layer 20B can be individually provided throughout the whole part in the front-back direction LD, and without folding back the constituent materials, the elastic film 30 may be interposed between the constituent material of the first sheet layer 20A and the constituent material of the second sheet layer 20B.

The elastic film 30 is not particularly limited, and any elastic thermoplastic resin film which has elasticity such as a non-porous film and a film having many holes or slits for ventilation can also be used. In particular, in the elastic film 30, the tensile strength in the width direction WD (stretchable direction ED, MD) is preferably 8 to 25 N/35 mm, the tensile strength in the front-back direction LD (direction XD orthogonal to the stretchable direction, CD) is preferably 5 to 20 N/35 mm, the tensile elongation in the width direction WD is preferably 450 to 1050%, and the tensile elongation in the front-back direction LD is preferably 450 to 1400%. The thickness of the elastic film 30 is not particularly limited, but it is preferably about 20 to 40 μm.

(Stretchable Region)

A region having the elastic film stretchable structure 20X in the outer member 20 has a stretchable region that is stretchable in the width direction WD. The stretchable region 80 has sections 32 in which, the elastic film 30 linearly continues along the width direction WD, and the stretchable region 80 contracted in the width direction WD due to a contraction force of the elastic film 30 is extensible in the width direction WD. More specifically, in a state where the elastic film 30 is stretched in the width direction WD, the first sheet layer 20A and the second sheet layer 20B are bonded via the bonding holes 31 of the elastic film 30 at intervals in the width direction WD and the front-back direction LD (direction XD orthogonal to the stretchable direction) orthogonal to the width direction WD. Further, in the stretchable region 80, by forming a large number of sheet bonded portions 40, the elastic film stretchable structure 20X is formed, and by arranging the bonding holes 31 so that the stretchable region 80 has the sections in which the elastic film 30 linearly continues along the width direction WD, such elasticity can be imparted.

Figure 10:
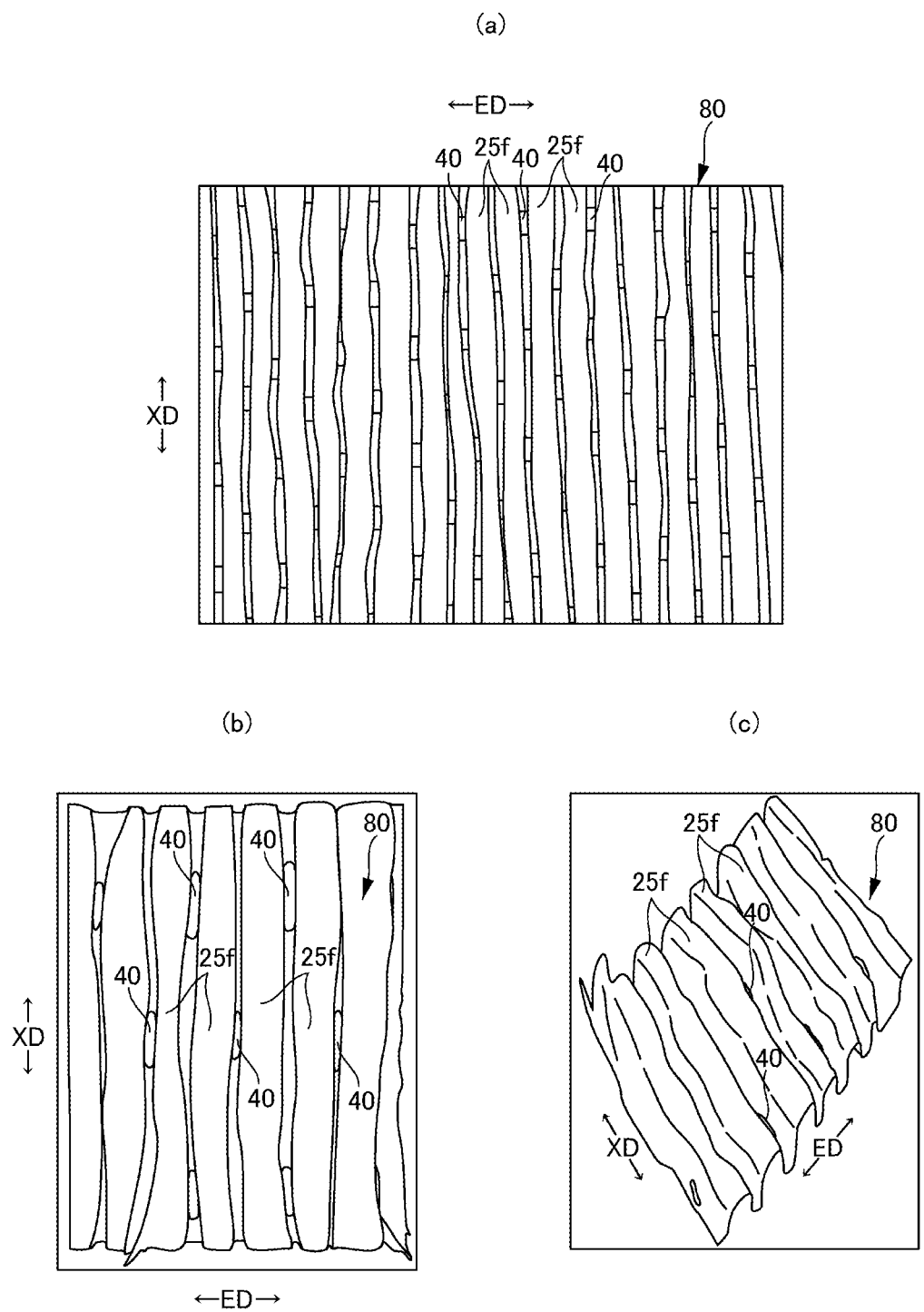
FIG. 10(a) is a plan view of a stretchable region.
FIG. 10(b) is an enlarged plan view of the stretchable region.
FIG. 10(c) is an enlarged perspective view of the stretchable region.

In a natural length state, as illustrated in FIG. 7(*d*), in the stretchable region 80, the first sheet layer 20A and the second sheet layer 20B between the sheet bonded portions 40 are raised in directions away from each other, and thus contraction wrinkles 25 extending in the front-back direction LD are formed. Further, as illustrated in FIG. 7(*c*), the contraction wrinkles 25 are still remained while being stretched even in a worn state stretched to some extent in the width direction WD. In addition, as in the illustrated embodiment, when neither the first sheet layer 20A nor the second sheet layer 20B is bonded to the elastic film 30 at least in a portion other than a portion between the first sheet layer 20A and the second sheet layer 20B at the sheet bonded portion 40, as can be seen from the FIG. 7(*c*) assuming the worn state and FIGS. 7(*a*) and 7(*b*) assuming the spread state of the first sheet layer 20A and the second sheet layer 20B, in these states, the gaps are formed between bonding holes 31 in the elastic film 30 and the sheet bonded portions 40, and even if a material of the elastic film 30 is a non-porous film and sheet, air permeability is imparted by the gaps. In addition, in the natural length state indicated in FIG. 7(*d*), the bonding holes 31 are narrowed by contraction of the elastic film 30, and the gaps are hardly formed between the bonding holes 31 and the sheet bonded portions 40. Note that the state of the contraction wrinkles 25 in a worn state and a natural length state can be found also in FIGS. 8 and 10.

Elongation at an elastic limit of the stretchable region 80 in the width direction WD is preferably 200% or more (preferably 265 to 295%). The elongation at the elastic limit of the stretchable region 80 is substantially determined by the stretch rate of the elastic film 30 at the time of manufacture. However, on the basis of this, the elongation at the elastic limit decreases due to a factor of inhibiting contraction in the width direction WD. The main inhibition factor is a ratio of the dimension 40*x* of the sheet bonded portion 40 to a unit length in the width direction WD, and the elongation at the elastic limit decreases as this ratio increases. In the usual case, since the dimension 40*x* of the sheet bonded portion 40 is correlated with the area rate of the sheet bonded portions 40, the elongation at the elastic limit of the stretchable region 80 can be adjusted by the area rate of the sheet bonded portions 40.

The stretching stress of the stretchable region 80 can be adjusted mainly by a sum of the widths 32*w* of the sections 32 in which the elastic film 30 linearly continues along the width direction WD. The width 32*w* of the section 32 in which the elastic film 30 linearly continues along the width direction WD is equal to a distance 31*d* of the two adjacent bonding holes 31 in the front-back direction LD coming into contact with both side edges of the above-mentioned section 32. The distance 31*d* between the two adjacent bonding holes 31 is equal to a distance 40*d* of the two adjacent sheet bonded portions 40 in the front-back direction LD coming into contact with the both side edges of the above-mentioned section when the length 31*y* of the bonding hole 31 in the front-back direction LD and the length 40y of the sheet bonded portion 40 in the front-back direction LD are equal (in the case of adopting for example, the above-described method where forming of the bonding holes 31 and forming of the sheet bonded portions 40 are performed simultaneously). Therefore, in this case, the stretching stress of the stretchable region 80 may be adjusted by the ratio of the length 40y of the sheet bonded portion 40 to a unit length in the front-back direction LD. In the usual case, since the length 40y of the sheet bonded portion 40 correlates with the area rate of the sheet bonded portions 40, the stretching stress of the stretchable region 80 can be adjusted by the area rate of the sheet bonded portions 40. The stretching stress in stretching to 50% of an elastic limit may be estimated as the stretching stress of the stretchable region 80.

The area rate of the sheet bonded portions 40 and the area of the individual sheet bonded portion 40 in the stretchable region 80 can be appropriately determined, but in the usual case, it is preferable to be within the following ranges.

The area of the sheet bonded portion 40: 0.14 to 3.5 mm$^2$ (particularly 0.14 to 1.0 mm$^2$)

The area rate of the sheet bonded portions 40: 1.8 to 19.1% (particularly 1.8 to 10.6%)

Figure 15:
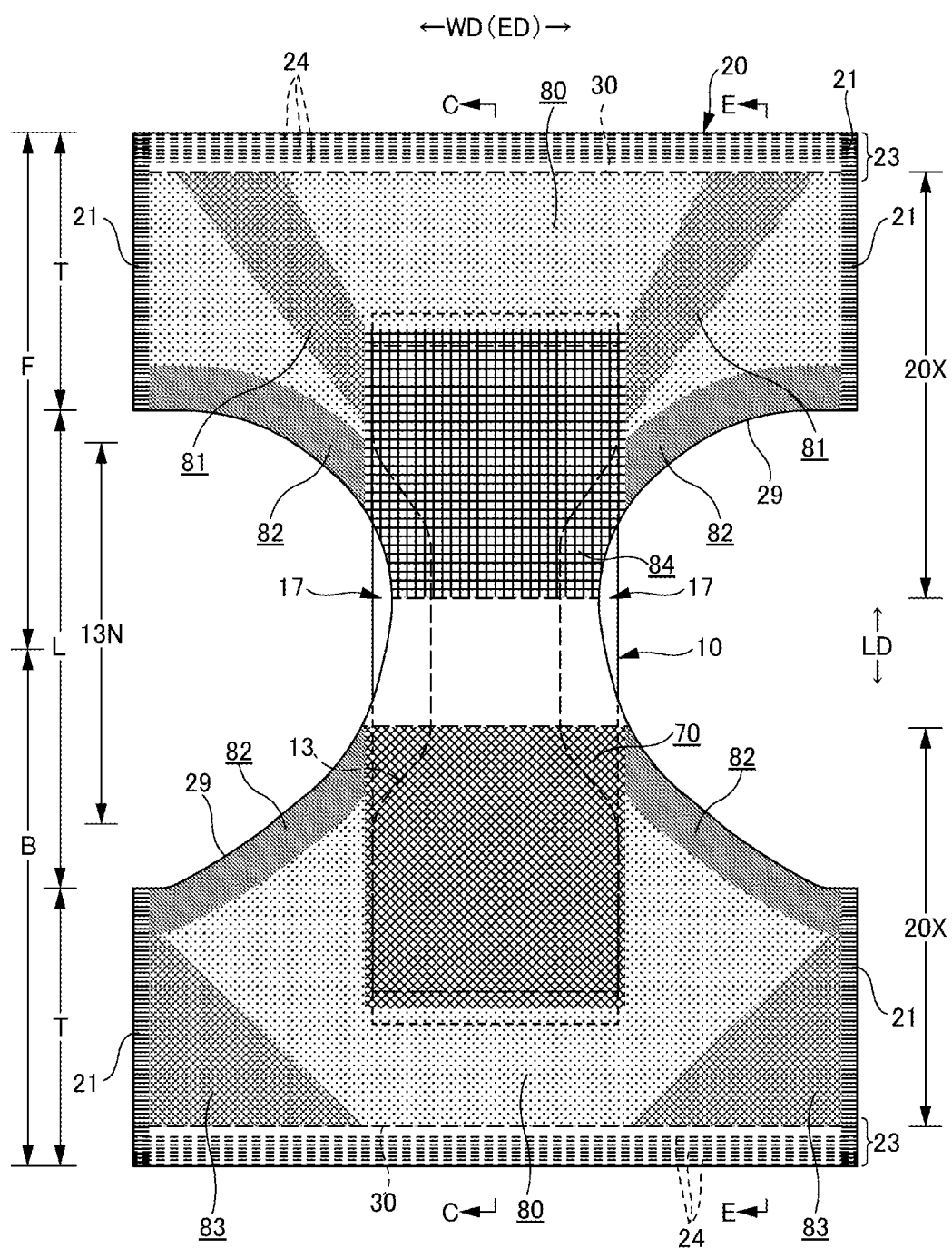
FIG. 15 is a plan view (external surface side) of an underpants-type disposable diaper in a spread state.
Figure 16:
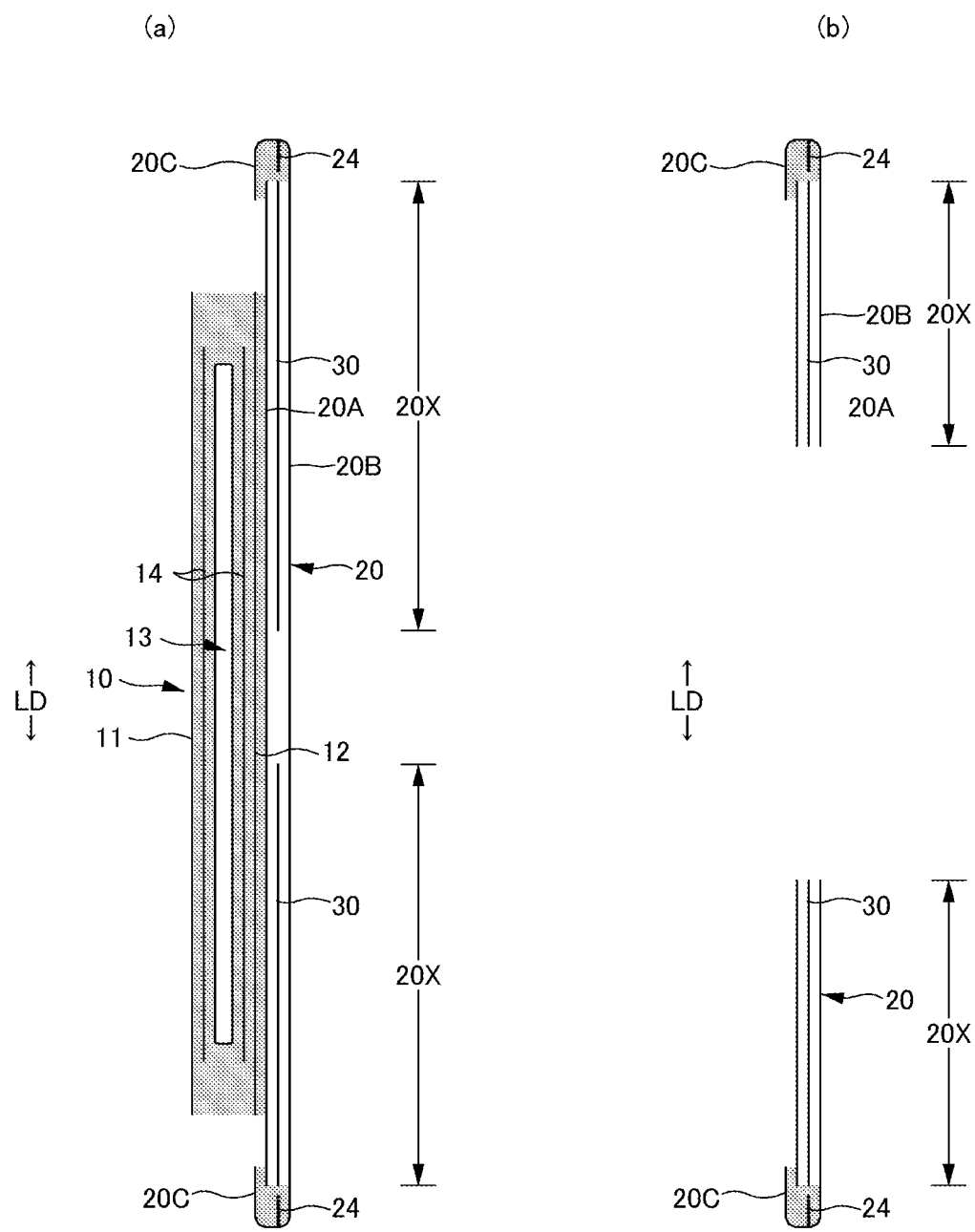
FIG. 16(a) is a cross-sectional view taken along line C-C of FIG. 15.
FIG. 16(b) is a cross-sectional view taken along line E-E of FIG. 15.

In this way, since the elongation at the elastic limit and the stretching stress of the stretchable region 80 can be adjusted by the area of the sheet bonded portion 40, as illustrated in FIG. 15, a plurality of regions having different area rate of the sheet bonded portions 40 in the stretchable region 80 is provided so that the fitting property can be adjusted depending on parts of the diaper. In the embodiment illustrated in FIG. 15, in the front body F, the area rates of the sheet bonded portions 40 in regions 81 extending obliquely along roots of legs and in edge regions 82 of the leg openings are higher than the area rates of the sheet bonded portions in the rest, and therefore these regions are flexibly stretchable due to the small stretching stress. In addition, in the back body B, the area rates of the sheet bonded portions 40 in iliac opposing regions 83 and in edge regions 82 of the leg openings are higher than the area rates of the sheet bonded portions in the rest, and therefore these regions are flexibly stretchable due to small stretching stress.

(Non-Stretchable Region)

As illustrated in FIG. 15, the non-stretchable region 70 can be provided on at least one side in the width direction of the stretchable region 80 in the region of the outer member 20 having the elastic film stretchable structure 20X. The arrangement of the stretchable region 80 and the non-stretchable region 70 can be appropriately determined. In the case of the outer member 20 of the underpants-type disposable diaper according to the present embodiment, since a part overlapping with the absorber 13 is a region unnecessary to stretch and contract, as the illustrated embodiment, a part or all of the portion overlapping with the absorber 13 (it is desirable to include substantially the entire inner and outer fixed regions 10B) is preferably the non-stretchable region 70. It is obvious that the non-stretchable region 70 can be provided from a region overlapping with the absorber 13 to a region not overlapping with the absorber 13 located in the width direction WD or the front-back direction LD thereof, or the non-stretchable region 70 can be provided only in the region not overlapping with the absorber 13.

The non-stretchable region 70 is configured, although the elastic film 30 continues in the width direction WD, so as not to have a part in which the elastic film 30 linearly continues along the width direction WD due to the presence of the bonding holes 31. Therefore, even though the elastic film stretchable structure 20X is configured as a whole to include both the stretchable region 80 and the non-stretchable region 70 by bonding the first sheet layer 20A and the second sheet layer 20B through the bonding holes 31 of the elastic film 30 to form the large number of sheet bonded portions 40 at intervals in the width direction WD and the front-back direction LD orthogonal thereto while the elastic film 30 is stretched in the width direction WD, in the non-stretchable region 70, the elastic film 30 does not linearly continue along the width direction WD, as illustrated in FIG. 13. Thus, the contraction force of the elastic film 30 hardly acts on the first sheet layer 20A and the second sheet layer 20B, and elasticity almost disappears, and the elongation at the elastic limit approaches 100%. In such non-stretchable region 70, the first sheet layer 20A and the second sheet layer 20B are bonded at a large number of sheet bonded portions 40 arranged at intervals, and the sheet bonded portions 40 are not continuous. Therefore, a decrease in flexibility is prevented. In other words, it is possible to form the stretchable region 80 and the non-stretchable region 70 depending on the presence or absence of a section in which the elastic film 30 does not linearly continue along the width direction WD. In addition, continuity of the elastic film 30 still remains in the non-stretchable region 70, since independent cut pieces of the elastic film 30 are not left, and wrinkles are not formed, appearance is extremely excellent, and the air permeability in the thickness direction by the bonding holes 31 is secured. In the non-stretchable region 70, the elongation at the elastic limit in the width direction WD is preferably 120% or less (preferably 110% or less, more preferably 100%).

Although the arrangement pattern of the bonding holes 31 in the elastic film 30 in the non-stretchable region 70 can be determined as appropriate, when staggered arrangement is adopted as illustrated in FIG. 13, if the center-to-center interval 31e of the two adjacent bonding holes 31 in the front-back direction LD is set to be shorter than the length 31y of the bonding hole 31 in the front-back direction LD, it is possible to almost completely eliminate the linear continuity in the width direction WD while maintaining the continuity of the elastic film 30, and the appearance is also preferable. In this case, it is more preferable that a center-to-center interval 31f of the two adjacent bonding holes 31 in the width direction WD is shorter than the length 31x of the bonding hole 31 in the width direction WD.

In the usual case, especially when the stretching stress is 4 to 12 N/35 mm in stretching the elastic film 30 four times in the width direction WD, in a state where the non-stretchable region 70 is stretched to the elastic limit in the width direction WD, it is preferable that the center-to-center interval 31e of the two adjacent bonding holes 31 in the front-back direction LD is 0.4 to 2.7 mm, and the length 31y of the bonding hole 31 in the front-back direction LD is 0.5 to 3.0 mm, particularly 0.7 to 1.1 mm. In addition, the center-to-center interval 31f of the two adjacent bonding holes 31 in the width direction WD is preferably 0.5 to 2 times, more preferably 1 to 1.2 times the length 31y of the bonding hole 31 in the front-back direction LD, and the length 31x of the bonding hole 31 in the width direction WD is preferably 1.1 to 1.8 times, particularly 1.1 to 1.4 times the center-to-center interval 31f of the two adjacent bonding holes 31 in the width direction WD. In a state where the non-stretchable region 70 is stretched to the elastic limit in the width direction WD (in other words, in a state where the first sheet layer 20A and the second sheet layer 20B are completely spread), the center-to-center interval 31f of the two adjacent bonding holes 31 in the width direction WD is equal to the center-to-center interval 40f of the two adjacent sheet bonded portions 40 in the width direction WD, the center-to-center interval 31*e* of the two adjacent bonding holes 31 in the front-back direction LD is equal to the center-to-center interval 40*e* of the two adjacent sheet bonded portions 40 in the front-back direction LD, and the length 31*y* of the bonding hole 31 in the front-back direction LD is equal to the length 40*y* of the seat bonded portion 40 in the front-back direction LD.

In a case in which neither the first sheet layer 20A nor the second sheet layer 20B is bonded to the elastic film 30 at least in a portion other than a portion between the first sheet layer 20A and the second sheet layer 20B at the sheet bonded portion 40 in the non-stretchable region 70, and the gaps, which are formed by the peripheral edge of the bonding hole 31 of the elastic film 30 and the sheet bonded portion 40 separated from each other, are included at both sides in the width direction of the sheet bonded portion 40 in the natural length state, it is preferable since air permeability is constantly added due to these gaps even if the material of the elastic film 30 is a non-porous film or a non-porous sheet. In the case of adopting the above-described method where forming of the bonding holes 31 and forming of the sheet bonded portions 40 are performed simultaneously, this state is obtained naturally irrespective of the shape of the sheet bonded portion 40 or the like.

The shape of the sheet bonded portion 40 and the bonding hole 31 in the natural length state is not particularly limited, but it is desirable that the area be small from the viewpoint of flexibility. To eliminate the linear continuity in the width direction WD of the elastic film 30, a shape that is long in the front-back direction LD is desirable. Therefore, an elliptical shape, a rectangular shape (refer to FIGS. 9(*e*) and 13(*a*)), a rhombus (refer to FIG. 9(*b*)), or a convex lens shape (refer to FIG. 9(*a*)), and a concave lens shape (refer to FIG. 9(*c*)) that are long in the front-back direction LD are preferable. However, if corners are acute as in a rhombus, the elastic film 30 tends to be fractured. In contrast, the convex lens shape is preferable in that the welding of the sheet bonded portions 40 is stabilized, and the concave lens shape is preferable in that the area can be further reduced.

The area rate of the sheet bonded portions 40 and the area of the individual sheet bonded portion 40 in the non-stretchable region can be appropriately determined, but in the usual case, it is preferable that the area is within the following range, since the non-stretchable region 70 is not hardened due to the small area of the sheet bonded portion 40 and the low area rate of the sheet bonded portions 40.

The area of the sheet bonded portion 40: 0.10 to 0.75 mm$^2$ (particularly 0.10 to 0.35 mm$^2$)

The area rate of the sheet bonded portions 40: 4 to 13% (especially 5 to 10%)

In this way, the elongation at the elastic limit of the non-stretchable region 70 can be changed by the arrangement pattern of the bonding holes 31, the dimension of the bonding hole 31, and the center-to-center interval of the two adjacent bonding holes. Therefore, although not illustrated, it is possible to make the elongation at the elastic limit different between a plurality of positions within the stretchable region 80 or between a plurality of the non-stretchable regions 70. For example, it is one preferable embodiment to set the elongation at the elastic limit in the non-stretchable region 70 of the front body F larger than the elongation at the elastic limit in the non-stretchable region 70 of the back body B.

It is possible to adopt other modes for eliminating elasticity: a mode where a non-stretchable region 70, although which has a section in which the elastic film linearly continues along the width direction WD similarly to the stretchable region, has the elongation at the elastic limit being remarkably low, specifically 130% or less, because the area rate of the sheet bonded portions is higher than that in the stretchable region; and a mode where the elastic film is cut at one or a plurality of places in the width direction WD as in a conventional stretchable structure using rubber threads, and so on.

(Vent Hole)

Characteristically, as illustrated in the example of the stretchable region 80 of FIG. 7 and the example of the non-stretchable region 70 of FIG. 13, the vent holes 33 are formed on the elastic film 30 at sites where the elastic film does not overlap with the sheet bonded portions 40, so that the air permeability is enhanced irrespective of the positions and number of the sheet bonded portions 40.

The shape of the vent hole 33 is not particularly limited, and it may be a perfect circle (illustrated form), an ellipse, a polygon such as a triangle, a rectangle, and a rhombus, a star shape, a cloud shape, a slit shape (that is not cut out but incised without any area, refer to FIG. 14) or the like. Although the size of the vent hole 33 is not particularly limited, if it is too small or too few, the effect of improving the air permeability is reduced, and if it is too large or too much, the peel strength of the first sheet layer 20A and the second sheet layer 20B may be lowered as will be described later. Therefore, as long as the vent hole 33 is not slit-shaped, the area of the vent hole 33 is preferably set to about 3 to 15% of the area of the sheet bonded portion 40, the area rate of the vent holes 33 in the natural state is preferably set to about 4.4 to 19.1%. In the case of the slit-shaped vent hole 33, the length of the vent hole 33 can be set to approximately 0.1 to 1 mm. Furthermore, the center-to-center interval of the adjacent two vent holes 33 in the stretchable direction ED and the center-to-center interval of the adjacent two vent holes 33 in the direction orthogonal to the stretchable direction ED can be set to about 1 to 2 mm.

Although the planar arrangement of the vent holes 33 can be appropriately determined, it is preferable to adopt a planar arrangement in which the vent holes 33 are regularly repeated as illustrated in FIG. 7. Similar to the arrangement of the sheet bonded portions 40 illustrated in FIG. 21, in addition to the regularly repeated arrangement such as an oblique lattice shape, a hexagonal lattice shape (they are also referred to as staggered lattice shape), a square lattice shape, a rectangular lattice shape, and a parallelotope lattice shape (a mode in which two groups are provided so that a large number of parallel oblique row groups intersect each other), etc. (including a mode in which these shapes are inclined at an angle of less than 90° with respect to the width direction). Additionally, it is also possible to adopt a planar arrangement in which a group of the vent holes 33 (arrangement of the group may be regular or irregular, and a pattern, a letter shape, etc. may be used) is regularly repeated.

The vent holes 33 can be formed by punching or needle sticking, and it is possible to adopt a manner in which the vent holes 33 are processed before forming the sheet bonded portions 40 (including using an already perforated elastic film), that is, the vent holes 33 are processed in a state of the elastic film 30 alone, and it is also possible to adopt another manner in which the vent holes 33 are processed after forming the sheet bonded portions 40, that is the vent holes 33 are processed in a state where the first sheet layer 20A, the elastic film 30 and the second sheet layer 20B are stacked.

In the case where the forming of the bonding holes 31 on the elastic film 30 and the forming of the sheet bonded portions 40 are performed at the same time through the welding by using the elastic film 30 on which the vent holes 33 have been already formed, as described before, as illustrated in FIG. 11, the elastic film 30 is stretched in a predetermined stretchable direction ED until it is sandwiched between the first sheet layer 20A and the second sheet layer 20B. Then, the elastic film 30 is sandwiched between the first sheet layer 20A and the second sheet layer 20B in a state where the vent holes 33 are stretched in the stretchable direction ED, and the sheet bonded portions 40 are formed through the welding on the outer member 20 as illustrated in FIG. 12(a). In the sheet bonded portion 40, at a site which overlaps with the vent hole 33, the first sheet layer 20A and the second sheet layer 20B are bonded to each other without interposing the melted and solidified material of the elastic film 30 therebetween. In addition, when only a part of the vent hole 33 overlaps with the sheet bonded portion 40, such vent hole 33 joins to the bonding hole 31, which has been formed while the sheet bonded portion 40 is formed. The stretching force exerting on the vent hole 33 positioned between the two adjacent sheet bonded portions 40 in the stretchable direction ED and the stretching force exerting on the vent hole 33 joined to the bonding hole 31 are partially released due to the forming of the sheet bonded portion 40, depending on the position of the vent hole 33. Thus, the vent hole 33 contracts in the stretchable direction ED accordingly. Then, when the outer member 20 is released from the stretched state after the welding so as to be in the natural length state, the bonding hole 31 closely contacts to a circumferential edge of the sheet bonded portion 40 as illustrated in FIG. 12(b) omitting the pleats, the vent hole 33 contracts in the stretchable direction ED so as to have a shape being substantially same as the shape before the stretching. Further, the vent hole 33 joined to the bonding hole 31 remains in an open state around the sheet bonded portion 40.

Here, when the first sheet layer 20A and the second sheet layer 20B are bonded via a melted and solidified material of the elastic film 30 (as an adhesive) rather than are bonded to each other directly through the welding, as described above, the peel strength is increased. However, when the size of the sheet bonded portion 40 is smaller than the size of the vent hole 33, when the position of the sheet bonded portion 40 and the position of the vent hole 33 overlap partially, the first sheet layer 20A and the second sheet layer 20B are bonded directly through the welding to each other over the entire sheet bonded portion 40, and the peel strength of the sheet bonded portion 40 may be lowered. On the other hand, as in the illustrated embodiment, in a state where the region having the elastic film stretchable structure 20X is stretched to have the elongation at the elastic limit in the stretchable direction ED, that is, in the same state as the state where the welding is performed, in the stretchable direction ED (at least either of the stretchable direction ED or the direction XD orthogonal to the stretchable direction ED), when the dimension 33x of the vent hole 33 is larger than the dimension 40x of the sheet bonded portion 40 (which is equal to the dimension of the protruding portion 60a of the anvil roll 60), as in the state where the welding is performed as illustrated in FIG. 22(a), at least a part of the sheet bonded portion 40 is necessarily bonded via the elastic film 30 when the welding is performed, such that the first sheet layer 20A and the second sheet layer 20B are not easily peeled off in the sheet bonded portion 40.

Figure 22:
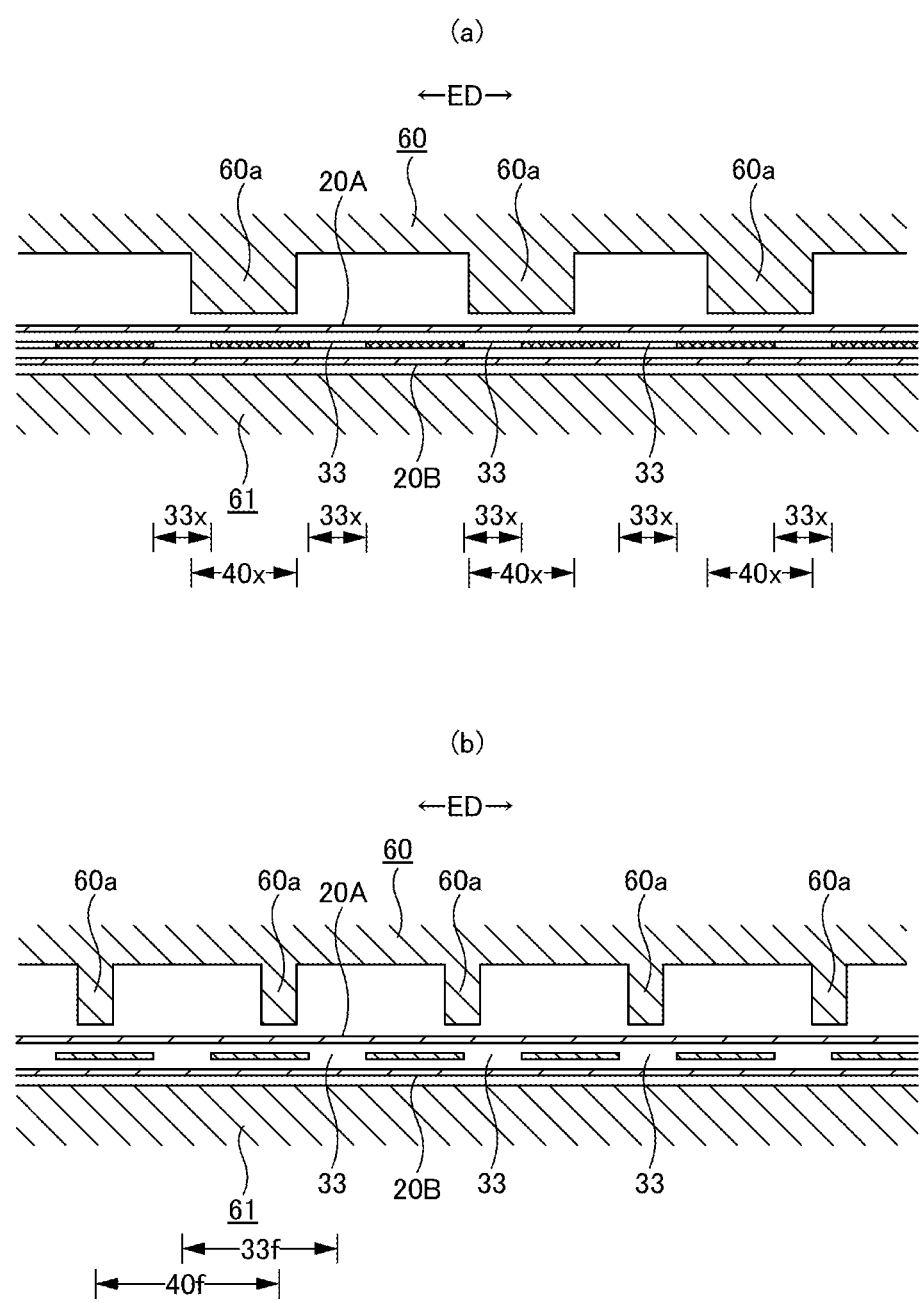
FIG. 22 is a cross-sectional view of a sheet bonding process.

In addition, when, for some reason, the dimension of the sheet bonded portion 40 has to be smaller than the dimension of the vent hole 33, as in the state where the welding is performed as illustrated in FIG. 22(b), in the stretchable direction ED (at least either of the stretchable direction ED or the direction XD orthogonal to the stretchable direction ED), the center-to-center interval 40f of the two adjacent sheet bonded portions 40 (which is equal to the interval in the MD of the two adjacent protruding portions 60a of the anvil roll 60) should be made larger than the center-to-center interval 33f of the two adjacent vent holes 33. As a result, the probability is decreased that the position of the sheet bonded portion 40 and the position of the vent hole 33 overlap, such that the peel strength hardly deteriorates.

Figure 11:
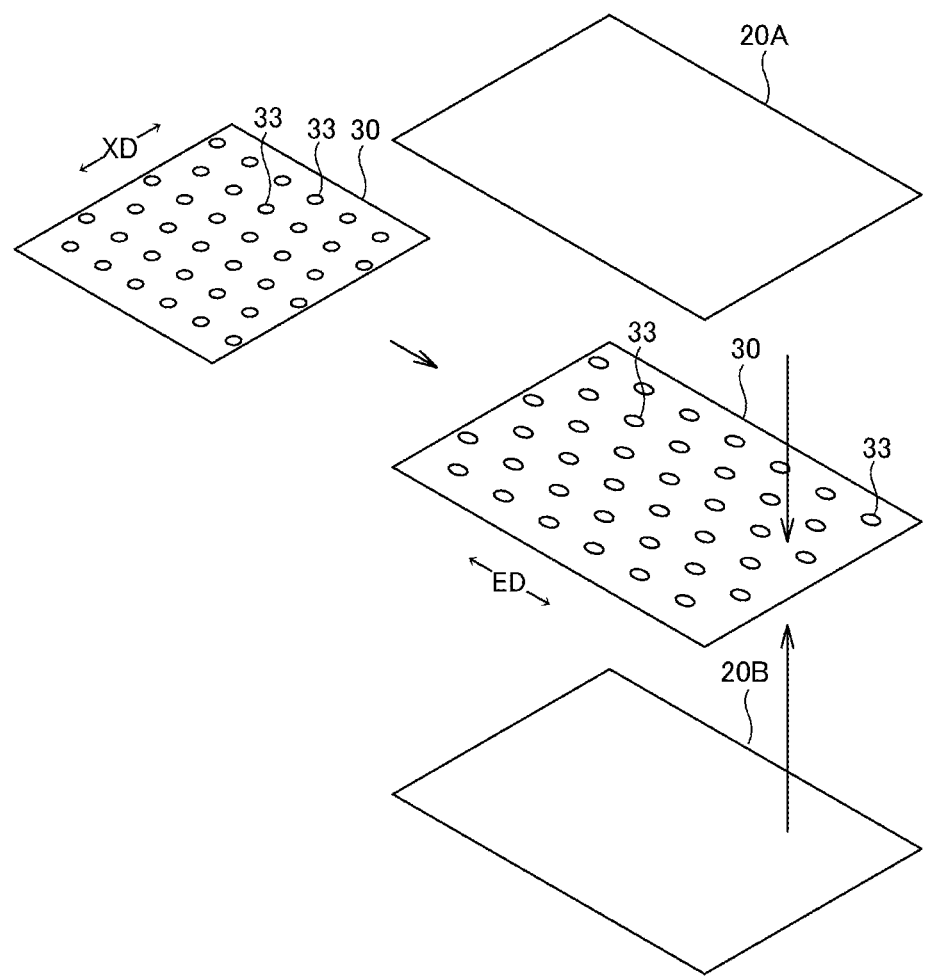
FIG. 11 is an assembled view of an elastic film stretchable structure.
Figure 14:
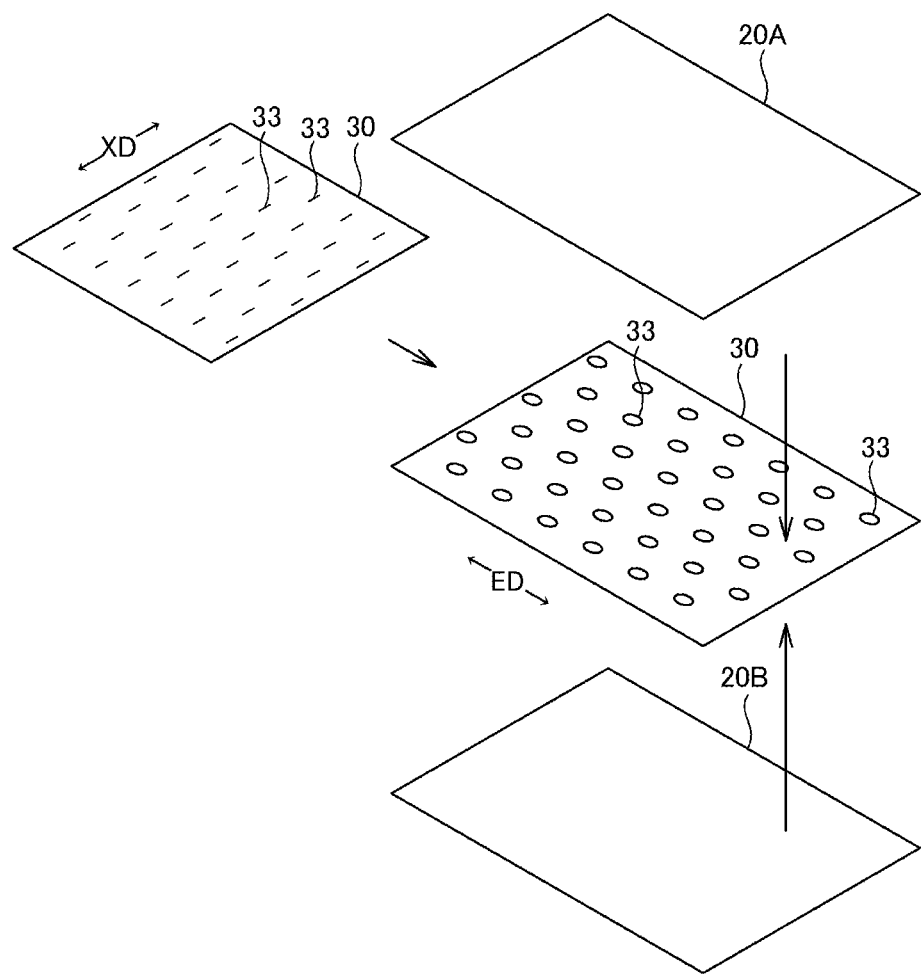
FIG. 14 is an assembled view of an elastic film stretchable structure.

Meanwhile, the embodiment illustrated in FIG. 11 is the case where the vent hole 33 has the area even when the elastic film 30 is in a natural length state, whereas the embodiment illustrated in FIG. 14 indicates the case where the vent hole 33 is slit-shaped. In this case, when the elastic film 30 is in the natural length state, the vent hole 33 has no area, but since the elastic film 30 is in the stretched state when the welding is performed, the slit opens to form the vent hole 33 having the area. In accordance with a location where the stretching force is released or the extent of releasing of the stretching force, the vent holes 33 contract in the stretchable direction ED, similarly to the embodiment illustrated in FIG. 11, but the slit-shaped vent holes are substantially closed depending on the positions thereof. In the non-stretchable region 70 illustrated in FIG. 13, almost all of the stretching force exerting on the elastic film 30 is released, so that all the vent holes 33 are in a closed state. In this way, by making the vent holes 33 slit-shaped, the probability is decreased that the first sheet layer 20A and the second sheet layer 20B are bonded directly through the welding at positions overlapping with the vent holes 33, and even in the case where the first sheet layer 20A and the second sheet layer 20B are directly bonded through the welding, the welding area is reduced. Therefore, the peel strength of the first sheet layer 20A and the second sheet layer 20B hardly deteriorates.

Figure 23:
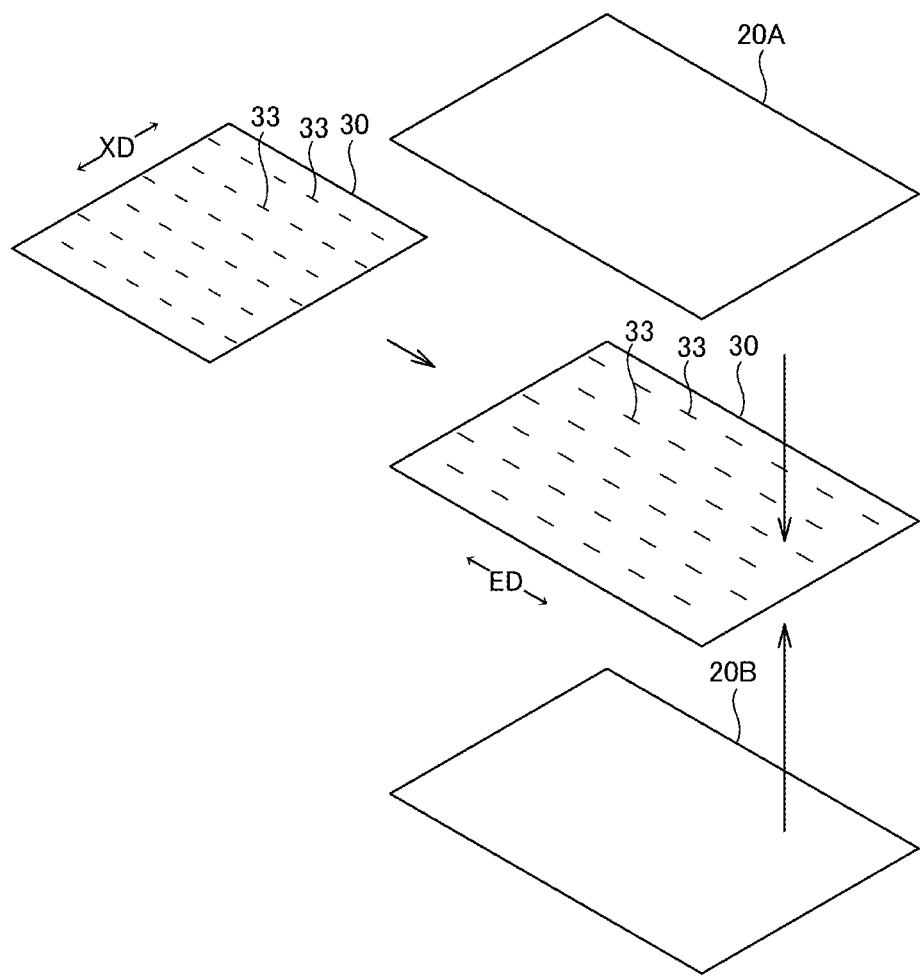
FIG. 23 is an assembled view of the elastic film stretchable structure.

Since the slit-like vent hole 33 in the illustrated embodiment is stretched in a direction intersecting with the stretchable direction ED, the area of the vent hole 33 increases in a stretched state, and the air permeability improves, whereas the probability is increased that the first sheet layer 20A and the second sheet layer 20B are bonded directly through the welding and thus the directly bonded area through the welding is increased. Therefore, as illustrated in FIG. 23, one preferable embodiment is that the direction of the slit-shaped vent hole 33 is set to the stretchable direction ED (that is, the longitudinal direction of the slit is along the stretchable direction ED). As a result, although the length of the vent hole 33 is increased in the stretched state, the area of the vent hole 33 hardly increases, and therefore the probability is decreased that the first sheet layer 20A and the second sheet layer 20B are bonded directly through the welding and thus the directly welded area is remarkably decreased.

The vent holes 33 are preferably provided in both of the stretchable region 80 and the non-stretchable region 70, but the vent holes 33 may be provided in only either one of the regions. Further, the vent holes 33 may have the same pattern in the stretchable region 80 and the non-stretchable region 70, or may have different patterns. Further, the numbers, the arrangements and the shapes of the vent holes 33 can be changed according to the positions of the vent holes 33. Although not illustrated, the vent holes 33 penetrating in the thickness direction may be formed in the first sheet layer 20A and the second sheet layer 20B at portions free of the sheet bonded portions 40.

<Explanation of Terms Used Herein>

The following terms in the specification have the following meanings unless otherwise specified in the specification.

"Front body" and "back body" mean front and back portions, respectively, with a center in the front-back direction of an underpants-type disposable diaper as a boundary. In addition, a crotch portion means a front-back direction range including the center in the front-back direction of an underpants-type disposable diaper, and in the case where an absorber has a narrowing portion, the crotch portion means a range in the front-back direction of a portion having the narrowing portion.

"Elongation at an elastic limit" means the elongation at the elastic limit in the stretchable direction ED (in other words, a state where the first sheet layer and the second sheet layer are completely spread), and expresses a length at the time of the elastic limit as a percentage when the natural length is assumed to be 100%.

"Area rate" means a rate of a target portion to a unit area and expresses the rate as a percentage by dividing a total area of the target portions (for example, the sheet bonded portions 40, the openings of the bonding holes 31, and the vent holes) in a target region (for example, the stretchable region 80, the non-stretchable region 70, a main elastic portion, and a damping elastic portion) by an area of the target region. In particular, an "area rate" in a region having a stretchable structure means an area rate in a state where it is stretched to the elastic limit in the stretchable direction ED. In an embodiment in which a large number of target portions are provided at intervals, it is desirable to obtain the area rate by using the target region of a size including ten or more target portions are included.

"Stretch rate" means a value relative to the natural length (100%).

"Basis weight" is measured as follows. After the sample or test piece is preliminarily dried, it is allowed to stand in a test room or apparatus under normal conditions (the test location is at a temperature of 20±5° C. and with a relative humidity of 65% or less) until the constant mass. The preliminary drying refers to making the sample or the test piece be constant mass in an environment not exceeding a temperature of 50° C. and a relative humidity of 10 to 25%. The fibers of an official moisture regain of 0.0% does not need preliminary drying. A cut sample with a size of 200 mm×250 mm (±2 mm) is cut from the test piece in the constant mass, with a cutting template (200 mm×250 mm, ±2 mm). The sample is weighed and the weight is multiplied by 20 into the weight per one square meter. The resulting value is defined as the basis weight.

"Thickness" of an absorber is measured using a thickness measuring apparatus of OZAKI MGF Co. Ltd. (PEACOCK, Dial Thickness Gauge Large Type, Model J-B (Measurement Range 0 to 35 mm) or Model K-4 (Measurement Range 0 to 50 mm)) by horizontally disposing a sample and the thickness measurement apparatus.

"Thickness" other than the above-described thickness is automatically determined with an automatic thickness gauge (KES-G5 handy compression measuring program) under the conditions of a load of 10 gf/cm$^2$ and a pressurization area of 2 cm$^2$.

"Tensile strength" and "tensile elongation (elongation at break)" are measured at an initial chuck interval (distance between marked lines) of 50 mm and a speed of testing of 300 mm/min according to JIS K7127: 1999 "Plastics—Determination of tensile properties", except that the test piece is a rectangle having a width of 35 mm×a length of 80 mm. As a tensile tester, for example, AUTOGRAPHAGS-G100N manufactured by SHIMADZU corporation can be used.

"Stretching stress" means a tensile stress (N/35 mm) measured when the sample is stretched in an elastic region by a tensile test at an initial chuck interval (distance between marked lines) of 50 mm and a speed of testing of 300 mm/min according to JIS K7127: 1999 "Plastics—Determination of tensile properties", and an extent of stretching may be appropriately determined depending on the test object. It is preferable that the test piece has a rectangular shape with a width of 35 mm and a length of 80 mm or more, but when a test piece with a width of 35 mm cannot be prepared, the test piece with a maximum possible width is prepared and the observed value is converted into a value at a width of 35 mm. Even if a sufficiently large test piece cannot be prepared from a target region with a small area, small test pieces can also be used for comparison of the stretching stress as long as the test pieces of the same size are used. As a tensile tester, for example, AUTOGRAPHAGS-G100N manufactured by SHIMADZU corporation can be used.

"Spread state" means a flatly spread state without contraction or slack.

Unless otherwise specified, dimensions of each portion refer to dimensions in the spread state, not in the natural length state.

In the absence of description about an environmental condition in a test or measurement, the test or measurement is performed in a test room or apparatus under normal conditions (the test location is at a temperature 20±5° C., relative humidity 65% or less).

INDUSTRIAL APPLICABILITY

As long as having a stretchable region which can apply the elastic film stretchable structure, the present invention can be applied to all disposable wearing articles such as tape-type and pad-type disposable diapers, sanitary napkins, disposable wearing articles for swimming and playing with water, in addition to the above-described underpants-type disposable diaper.

REFERENCE SIGNS LIST 10 inner member
10B inner and outer fixed region
11 liquid pervious top sheet
12 liquid impervious sheet
13 absorber
13N narrowing portion
14 wrapping sheet
17 free-absorber side portion
20 outer member
20A first sheet layer
20B second sheet layer
20C folded portion
20X elastic film stretchable structure
21 side seal portion
23 waist portion
24 waist elastic member
25 contraction wrinkle
29 leg line
30 elastic film
31 bonding hole
40 sheet bonded portion
70 non-stretchable region
80 stretchable region 90 three-dimensional gather
93 fallen portion
94 free portion
95 gather sheet
96 elastic gather member
B back body
ED stretchable direction
F front body
L intermediate portion
LD front-back direction
T lower torso portion
WD width direction
33 vent hole

The invention claimed is:

1. A disposable wearing article, having an elastic film stretchable structure in which an elastic film is stacked between a first sheet layer having air permeability and a second sheet layer having air permeability, the first sheet layer and the second sheet layer are bonded through bonding holes penetrating the elastic film at a plurality of sheet bonded portions arranged at intervals,
 wherein a region having the elastic film stretchable structure includes a stretchable region that is stretchable in a stretchable direction,
 the stretchable region is contracted in the stretchable direction by a contraction force of the elastic film and is extensible in the stretchable direction,
 each of the bonding holes is bounded by a circumferential edge, wherein areas of the elastic film inclusive of and inside of each of the circumferential edges collectively comprise a bonding hole region;
 vent holes are provided on the elastic film at sites where the elastic film does not overlap with the sheet bonded portions; and
 wherein at least a portion of the vent holes are wholly formed at sites outside of the bonding hole region.

2. The disposable wearing article according to claim 1, wherein
 each of the first sheet layer and the second sheet layer is a nonwoven fabric,
 the first sheet layer and the second sheet layer are bonded through the bonding holes penetrating the elastic film at the plurality of sheet bonded portions arranged at intervals,
 the first sheet layer and the second sheet layer are bonded to each other via a melted and solidified material of the elastic film in at least a part of the sheet bonded portions, and
 a dimension of the sheet bonded portions is larger than a dimension of the vent hole in at least one of the stretchable direction and a direction orthogonal to the stretchable direction in a state where the region having the elastic film stretchable structure is stretched to have elongation at an elastic limit in the stretchable direction.

3. The disposable wearing article, according to claim 1, wherein
 each of the first sheet layer and the second sheet layer is a nonwoven fabric,
 the first sheet layer and the second sheet layer are bonded through the bonding holes formed on the elastic film at the plurality of sheet bonded portions arranged at intervals,
 the first sheet layer and the second sheet layer are bonded to each other via a melted and solidified material of the elastic film in at least a part of the sheet bonded portions,
 a dimension of the sheet bonded portions is smaller than a dimension of the vent hole, and a center-to-center interval of the two adjacent sheet bonded portions is larger than a center-to-center interval of the two adjacent vent holes in at least one of the stretchable direction and a direction orthogonal to the stretchable direction in a state where the region having the elastic film stretchable structure is stretched to have elongation at an elastic limit in the stretchable direction.

4. The disposable wearing article according to claim 1, wherein the vent hole has a slit shape in a natural length state of the elastic film.

5. The disposable wearing article according to claim 1, wherein the disposable wearing article is an underpants type disposable wearing article including an outer member disposed in a front body and a back body provided as one unit or an outer member disposed in the front body and the back body provided separately, an inner member, which is attached to a center portion in a width direction of the outer member and provided to dispose from a front side of a crotch portion through the crotch portion to a back side of the crotch portion, side seal portions into which both side portions of the outer member in the front body and both side portions of the outer member in the back body are bonded respectively, a waist opening, and a pair of right and left leg openings,
 wherein the outer member in at least one of the front body and the back body is provided with the elastic film stretchable structure having a range in the width direction, which is corresponding to a distance between both the side seal portions and a range in a front-back direction, which is corresponding to at least a part of the side seal portion, so that the stretchable direction of the stretchable region is arranged in the width direction.

6. The disposable wearing article according claim 2, wherein the vent hole has a slit shape in a natural length state of the elastic film.

7. The disposable wearing article according to claim 3, wherein the vent hole has a slit shape in a natural length state of the elastic film.

8. The disposable wearing article according to claim 2, wherein the disposable wearing article is an underpants type disposable wearing article including an outer member disposed in a front body and a back body provided as one unit or an outer member disposed in the front body and the back body provided separately, an inner member, which is attached to a center portion in a width direction of the outer member and provided to dispose from a front side of a crotch portion through the crotch portion to a back side of the crotch portion, side seal portions into which both side portions of the outer member in the front body and both side portions of the outer member in the back body are bonded respectively, a waist opening, and a pair of right and left leg openings,
 wherein the outer member in at least one of the front body and the back body is provided with the elastic film stretchable structure having a range in the width direction, which is corresponding to a distance between both the side seal portions and a range in a front-back direction, which is corresponding to at least a part of the side seal portion, so that the stretchable direction of the stretchable region is arranged in the width direction.

9. The disposable wearing article according to claim 3, wherein the disposable wearing article is an underpants type disposable wearing article including an outer member disposed in a front body and a back body provided as one unit or an outer member disposed in the front body and the back body provided separately, an inner member, which is attached to a center portion in a width direction of the outer member and provided to dispose from a front side of a crotch portion through the crotch portion to a back side of the crotch portion, side seal portions into which both side portions of the outer member in the front body and both side portions of the outer member in the back body are bonded respectively, a waist opening, and a pair of right and left leg openings, wherein the outer member in at least one of the front body and the back body is provided with the elastic film stretchable structure having a range in the width direction, which is corresponding to a distance between both the side seal portions and a range in a front-back direction, which is corresponding to at least a part of the side seal portion, so that the stretchable direction of the stretchable region is arranged in the width direction.

10. The disposable wearing article according to claim 4, wherein the disposable wearing article is an underpants type disposable wearing article including an outer member disposed in a front body and a back body provided as one unit or an outer member disposed in the front body and the back body provided separately, an inner member, which is attached to a center portion in a width direction of the outer member and provided to dispose from a front side of a crotch portion through the crotch portion to a back side of the crotch portion, side seal portions into which both side portions of the outer member in the front body and both side portions of the outer member in the back body are bonded respectively, a waist opening, and a pair of right and left leg openings, wherein the outer member in at least one of the front body and the back body is provided with the elastic film stretchable structure having a range in the width direction, which is corresponding to a distance between both the side seal portions and a range in a front-back direction, which is corresponding to at least a part of the side seal portion, so that the stretchable direction of the stretchable region is arranged in the width direction.

* * * * *